(12) United States Patent
Hohla

(10) Patent No.: US 6,575,962 B2
(45) Date of Patent: *Jun. 10, 2003

(54) APPARATUS FOR MODIFYING THE SURFACE OF THE EYE THROUGH LARGE BEAM LASER POLISHING AND METHOD OF CONTROLLING THE APPARATUS

(75) Inventor: Kristian Hohla, Vaterstetten (DE)

(73) Assignee: Technolas GmbH Ophthalmologische Systeme, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/177,442

(22) Filed: Oct. 21, 1998

(65) Prior Publication Data

US 2002/0099362 A1 Jul. 25, 2002

Related U.S. Application Data

(60) Continuation of application No. 08/487,281, filed on Jun. 7, 1995, now Pat. No. 5,827,262, which is a division of application No. 08/338,495, filed as application No. PCT/EP93/02667 on Sep. 30, 1993, now Pat. No. 5,683,379.

(30) Foreign Application Priority Data

Oct. 1, 1992 (DE) .......................................... 42 32 915

(51) Int. Cl.[7] .............................................. A61F 9/07
(52) U.S. Cl. ................................ 606/5; 606/3; 606/10; 606/12
(58) Field of Search ............................. 606/3, 5, 10–13

(56) References Cited

U.S. PATENT DOCUMENTS 5,683,379 A * 11/1997 Hohla ........................... 606/5

FOREIGN PATENT DOCUMENTS

EP 280414 * 8/1988 ..................... 606/5

OTHER PUBLICATIONS

American Heritage Dictionary, Houghton Mifflin Co. Boston 1982 pp 146 & 1095.*

* cited by examiner

Primary Examiner—David M. Shay
(74) Attorney, Agent, or Firm—William Greener

(57) ABSTRACT

A apparatus and method for controlling an apparatus for removing tissue from the eye performs various types of corrections using a relatively large beam, but oscillating, or dithering, that being to prevent reinforcing ridges from being formed during the tissue removal process. Further, various types of correction, such as hyperopia and astigmatism correction, are performed using a large beam that is scanned over the area to be ablated using overlapping shots. Further, the epithelium in the area to be treated is removed using an infrared fluorescent dye to dye the epithelium, and then observing the fluorescent patterns from the epithelium area to be removed. Once a certain area is no longer fluorescent after laser shots, smaller shots are then applied, selectively removing the epithelium from the remaining regions. Again, the fluorescence patterns are observed, and the process is repeated until no epithelium remains. At this point, all of the epithelium is removed, and further a map is created of the initial epithelial thickness at each point in the area from which the epithelium was removed.

36 Claims, 29 Drawing Sheets

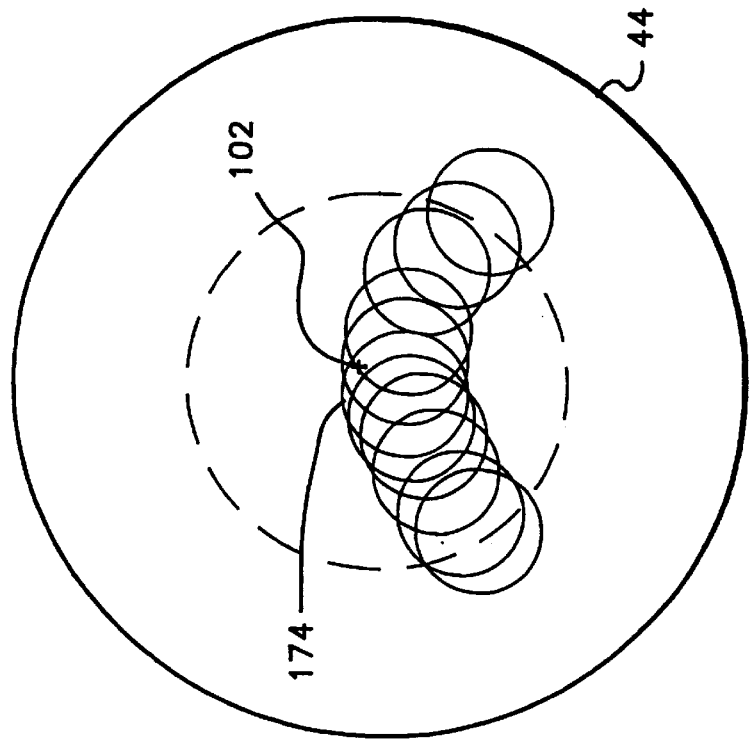
FIG. 5
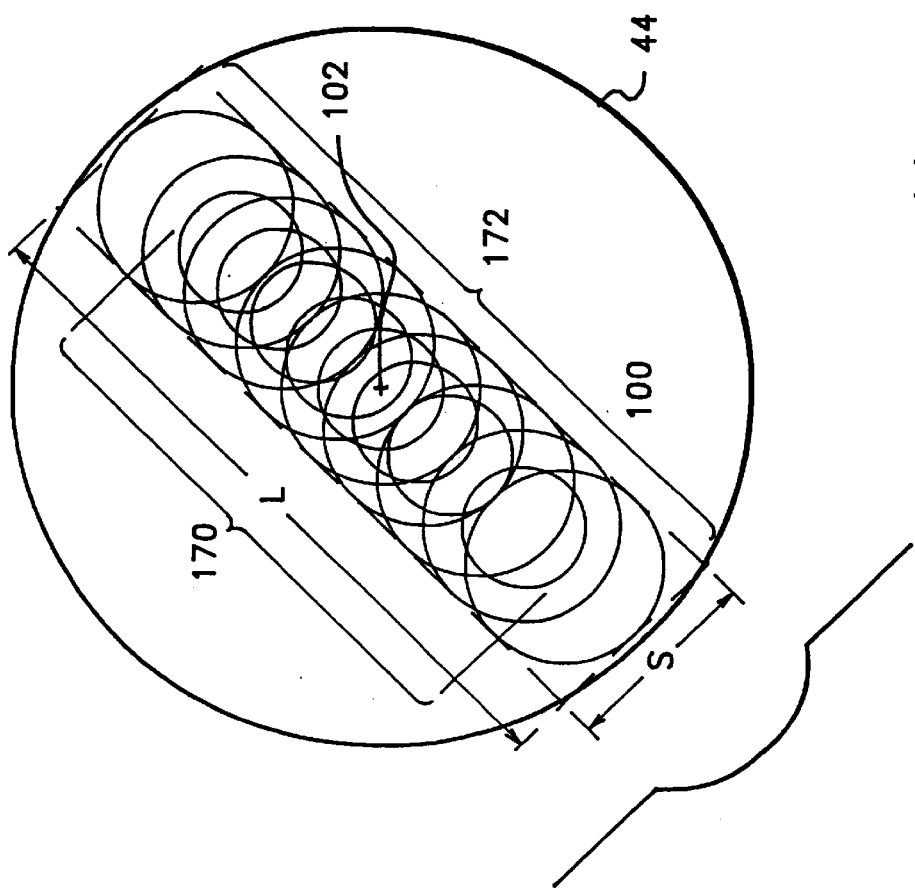
FIG. 4A
FIG. 4B

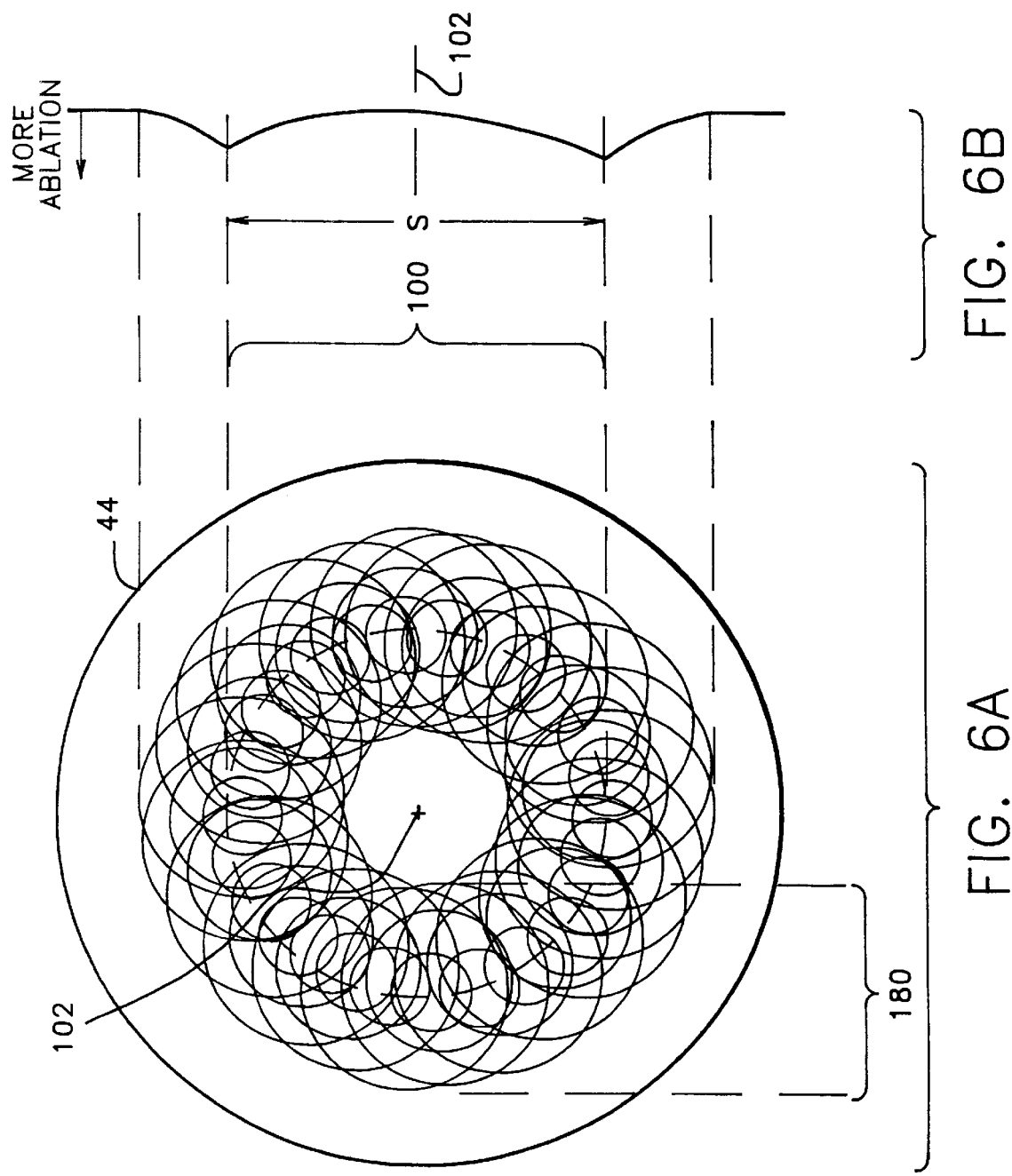

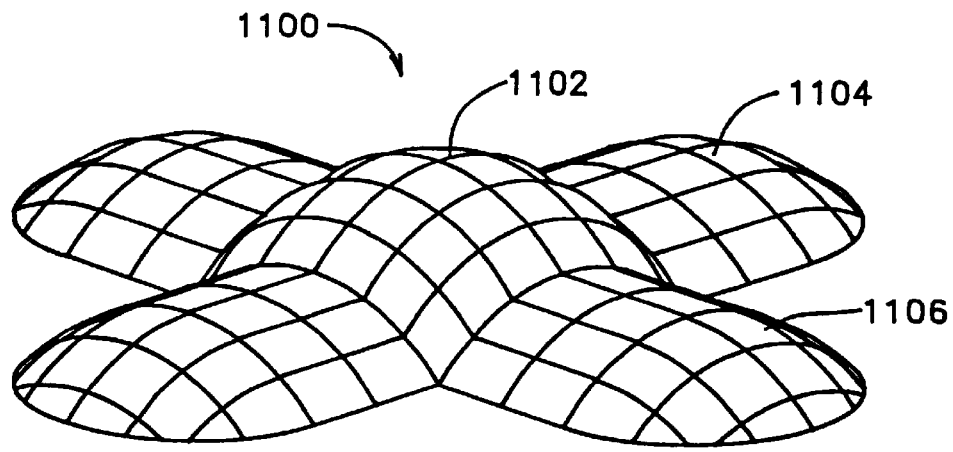
FIG. 17
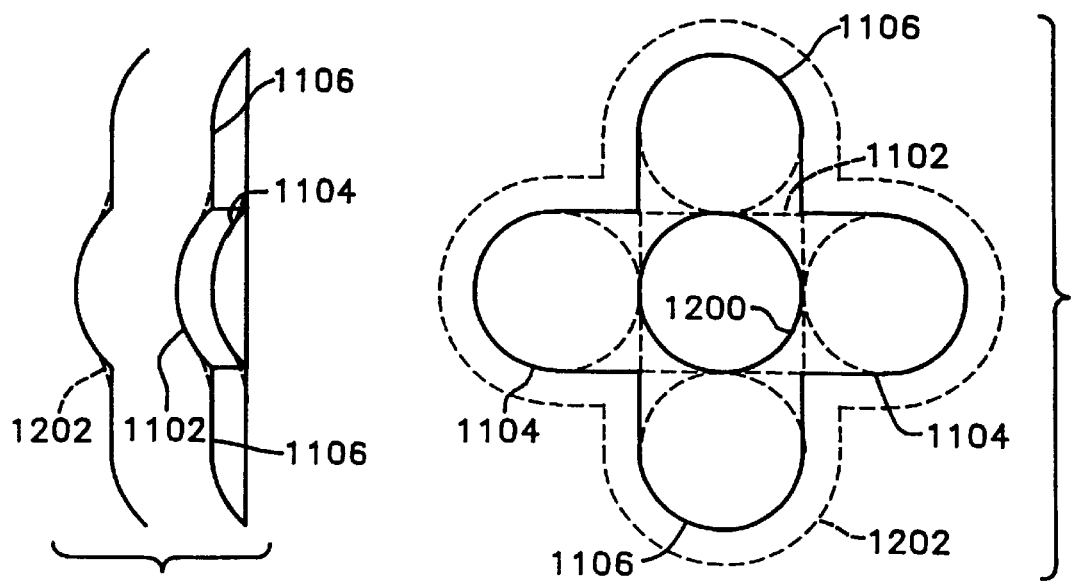
FIG. 18C
FIG. 18A
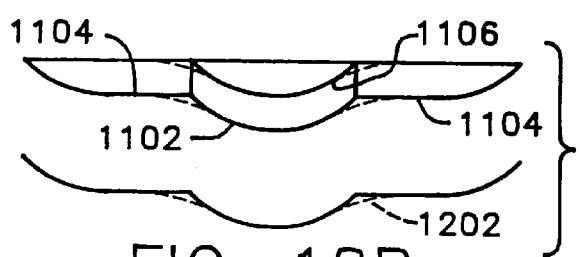
FIG. 18B

| No. | x_pos | y_pos | No. | x_pos | y_pos | No. | x_pos | y_pos |
|---|---|---|---|---|---|---|---|---|
| 5 | -1953 | 0 | 116 | -793 | -562 | 106 | -364 | 955 |
| 22 | -1665 | -331 | 130 | -789 | 380 | 215 | -360 | 104 |
| 14 | -1664 | -689 | 146 | -779 | -44 | 193 | -343 | -343 |
| 13 | -1664 | 689 | 78 | -738 | -981 | 199 | -343 | 343 |
| 30 | -1580 | 314 | 122 | -706 | 596 | 155 | -336 | -650 |
| 46 | -1461 | 123 | 154 | -697 | -222 | 20 | -331 | 1665 |
| 38 | -1450 | 507 | 15 | -689 | -1664 | 216 | -328 | -181 |
| 21 | -1412 | 943 | 12 | -689 | 1664 | 32 | -314 | -1580 |
| 39 | -1384 | -666 | 139 | -688 | -460 | 223 | -314 | 9 |
| 54 | -1382 | -235 | 91 | -675 | 897 | 129 | -289 | 827 |
| 6 | -1381 | -1381 | 101 | -668 | -838 | 178 | -283 | -513 |
| 4 | -1381 | 1381 | 161 | -667 | 152 | 191 | -272 | 462 |
| 31 | -1339 | -895 | 37 | -666 | 1384 | 231 | -241 | -55 |
| 69 | -1276 | 144 | 153 | -650 | 336 | 52 | -235 | 1382 |
| 61 | -1254 | 479 | 169 | -636 | -18 | 224 | -228 | -216 |
| 62 | -1225 | -548 | 124 | -598 | -706 | 160 | -222 | 697 |
| 77 | -1216 | -172 | 145 | -582 | 520 | 201 | -218 | -370 |
| 53 | -1143 | 811 | 162 | -579 | -364 | 222 | -216 | 228 |
| 47 | -1120 | -946 | 177 | -563 | -162 | 230 | -209 | 131 |
| 92 | -1112 | 157 | 114 | -562 | 793 | 214 | -181 | 328 |
| 85 | -1086 | -450 | 60 | -548 | 1225 | 75 | -172 | 1216 |
| 84 | -1086 | 450 | 147 | -520 | -582 | 117 | -163 | -958 |
| 100 | -1065 | -120 | 192 | -519 | 134 | 140 | -162 | -812 |
| 70 | -1004 | -801 | 184 | -513 | 283 | 183 | -162 | 563 |
| 76 | -981 | 738 | 40 | -507 | -1450 | 238 | -160 | 51 |
| 115 | -958 | 163 | 200 | -485 | 0 | 94 | -157 | -1112 |
| 108 | -955 | -364 | 63 | -479 | -1254 | 163 | -152 | -667 |
| 45 | -946 | 1120 | 185 | -462 | -272 | 239 | -149 | -77 |
| 23 | -943 | -1412 | 176 | -462 | 437 | 71 | -144 | -1276 |
| 107 | -933 | 417 | 137 | -460 | 688 | 186 | -134 | -519 |
| 123 | -921 | -78 | 86 | -450 | -1086 | 232 | -131 | -209 |
| 93 | -897 | -675 | 83 | -450 | 1086 | 48 | -123 | -1461 |
| 29 | -895 | 1339 | 170 | -437 | -462 | 98 | -120 | 1085 |
| 99 | -838 | 668 | 109 | -417 | -933 | 206 | -107 | 416 |
| 131 | -827 | -289 | 208 | -416 | -107 | 209 | -104 | -360 |
| 138 | -812 | 162 | 132 | -380 | -789 | 121 | -78 | 921 |
| 55 | -811 | -1143 | 207 | -370 | 218 | 237 | -77 | 149 |
| 68 | -801 | 1004 | 168 | -364 | 579 | 229 | -65 | 241 |

FIG. 24A

| No. | x_pos | y_pos | No. | x_pos | y_pos | No. | x_pos | y_pos |
|---|---|---|---|---|---|---|---|---|
| 240 | -51 | -160 | 113 | 163 | 958 | 151 | 520 | 582 |
| 152 | -44 | 779 | 79 | 172 | -1216 | 64 | 548 | -1225 |
| 246 | -31 | 2 | 210 | 181 | -328 | 118 | 562 | -793 |
| 247 | -23 | -21 | 226 | 209 | -131 | 181 | 563 | 162 |
| 245 | -21 | 23 | 218 | 216 | -228 | 166 | 579 | 364 |
| 175 | -18 | 636 | 205 | 218 | 370 | 149 | 582 | -520 |
| 250 | -15 | 10 | 156 | 222 | -697 | 128 | 596 | 706 |
| 217 | -9 | -314 | 220 | 228 | 216 | 173 | 636 | 18 |
| 248 | -2 | -31 | 56 | 235 | -1382 | 157 | 650 | -336 |
| 7 | 0 | -1953 | 227 | 241 | 55 | 33 | 666 | -1384 |
| 194 | 0 | -485 | 187 | 272 | -462 | 165 | 667 | -152 |
| 198 | 0 | 485 | 182 | 283 | 513 | 97 | 668 | 838 |
| 3 | 0 | 1953 | 133 | 289 | -827 | 95 | 675 | -897 |
| 244 | 2 | 31 | 219 | 314 | -9 | 143 | 688 | -460 |
| 221 | 9 | 314 | 28 | 314 | 1580 | 16 | 689 | -1664 |
| 249 | 15 | -10 | 212 | 328 | 181 | 11 | 689 | 1664 |
| 171 | 18 | -636 | 24 | 331 | -1665 | 158 | 697 | 222 |
| 241 | 21 | -23 | 159 | 336 | 650 | 126 | 706 | -596 |
| 243 | 23 | 21 | 195 | 343 | -343 | 74 | 738 | 981 |
| 242 | 31 | -2 | 197 | 343 | 343 | 150 | 779 | 44 |
| 148 | 44 | -779 | 211 | 360 | -104 | 134 | 789 | -380 |
| 236 | 51 | 160 | 110 | 364 | -955 | 120 | 793 | 562 |
| 225 | 55 | -241 | 164 | 364 | -579 | 72 | 801 | -1004 |
| 233 | 77 | -149 | 203 | 370 | -218 | 51 | 811 | 1143 |
| 125 | 78 | -921 | 136 | 380 | 789 | 142 | 812 | -162 |
| 213 | 104 | 360 | 204 | 416 | 107 | 135 | 827 | 289 |
| 202 | 107 | -416 | 105 | 417 | 933 | 103 | 838 | -668 |
| 102 | 120 | -1065 | 174 | 437 | 462 | 25 | 895 | -1339 |
| 44 | 123 | 1461 | 87 | 450 | -1086 | 89 | 897 | 675 |
| 228 | 131 | 209 | 82 | 450 | 1086 | 127 | 921 | 78 |
| 190 | 134 | 519 | 141 | 460 | -688 | 111 | 933 | -417 |
| 67 | 144 | 1276 | 172 | 462 | -437 | 19 | 943 | 1412 |
| 235 | 149 | 77 | 189 | 462 | 272 | 41 | 946 | -1120 |
| 167 | 152 | 667 | 59 | 479 | 1254 | 112 | 955 | 364 |
| 90 | 157 | 1112 | 196 | 485 | 0 | 119 | 958 | -163 |
| 234 | 160 | -51 | 36 | 507 | 1450 | 80 | 981 | -738 |
| 179 | 162 | -563 | 180 | 513 | -283 | 86 | 1004 | 801 |
| 144 | 162 | 812 | 188 | 519 | -134 | 104 | 1065 | 120 |

FIG. 24B

| No. | x_pos | y_pos |
|---|---|---|
| 88 | 1086 | -450 |
| 81 | 1086 | 450 |
| 96 | 1112 | -157 |
| 43 | 1120 | 946 |
| 49 | 1143 | -811 |
| 73 | 1216 | 172 |
| 58 | 1225 | 548 |
| 57 | 1254 | -479 |
| 65 | 1276 | -144 |
| 27 | 1339 | 895 |
| 8 | 1381 | -1381 |
| 2 | 1381 | 1381 |
| 50 | 1382 | 235 |
| 35 | 1384 | 666 |
| 17 | 1412 | -943 |
| 34 | 1450 | -507 |
| 42 | 1461 | -123 |
| 26 | 1580 | -314 |
| 9 | 1664 | -689 |
| 10 | 1664 | 689 |
| 18 | 1665 | 331 |
| 1 | 1953 | 0 |

FIG. 24C

APPARATUS FOR MODIFYING THE SURFACE OF THE EYE THROUGH LARGE BEAM LASER POLISHING AND METHOD OF CONTROLLING THE APPARATUS

This application is a Continuation of U.S. application Ser. No. 08/487,281 filed on Jun. 7, 1995, now U.S. Pat. No. 5,827,262, which was Divisional of U.S. application Ser. No. 08/338,495 filed on Nov. 16, 1994, now U.S. Pat. No. 5,683,379, which was the national stage of PCT/EP93/02667, filed Sep. 30, 1993, all of which are hereby incorporated by reference.

BACKGROUND OF THE INVENTION

1. Field of the Invention

The invention relates to an apparatus for surgically modifying the curvature of the eye cornea and a method of controlling the apparatus, and more particularly to an apparatus for smoothly correcting a variety of corneal defects and a method of controlling the apparatus.

2. Description of the Related Art

Since the initial development of corrective lenses, new and better ways of correcting defective eyesight have been developed. From the bifocal lens and extended wear soft contact lens to corneal incisions and shaping, the field of ophthalmology has seen great advances in convenience, safety, and accuracy in correcting a variety of sight defects, including myopia, hyperopia, and astigmatism.

While corrective lenses still find wide general application, ophthalmologists are focussing on surgery to correct such defects. One of the most popular surgical techniques is radial keratotomy, in which a surgeon forms radial slits in the outer surface of the cornea, allowing the cornea to re-shape and resulting in a modified cornea to correct the deficiencies of the patient's sight. This technique has continued to develop, but the advent of the laser and its introduction into the field of medicine have given rise to a new and potentially revolutionary method of eye surgery. Specifically, the development of the excimer laser and its application to eye surgery has opened a new approach to ophthalmological surgery.

The excimer laser produces coherent light of a very short wavelength of around 193 nm. At these wavelengths and the resulting high energies, the excimer laser removes, or ablates, tissue at the molecular level without significant heating of adjacent tissue. Thus, rather than "burning" away tissue, the excimer laser literally breaks the molecular bonds, and the ablated tissue is ejected from the ablated surface leaving a relatively unmarred surface to heal virtually scar-free. This aspect of the excimer laser is now well known and is further described, for example, in U.S. Pat. No. 4,784,135 entitled "Far Ultraviolet Surgical and Dental Procedures," issued Nov. 15, 1988.

The word "excimer" in excimer laser was initially drawn from its molecular principal of operation. The excimer laser was initially based on the lasing action of excited dimers, such as xenon, krypton, or fluorine in the form of $Xe_2$, $Kr_2$, or $F_2$. The word "excimer" as applied to lasers is now a misnomer, as the most popular excimer laser used in eye surgery does not even use dimers—it uses argon fluoride. The excimer laser is also a pumped laser, in the sense that another laser is used to stimulate the lasing action of the argon fluoride mixture in the laser cavity. "Eximer laser" has now come to be applied to an entire group of lasers with ultraviolet wavelengths below 400 nm.

When used in ophthalmological surgery, the eximer laser is preferably pulsed, as that allows for application of high energies without thermal heating. These pulses are very short bursts of high energy laser light applied to the cornea. For example, such a laser is typically pulsed at between 1 to 50 Hz with a 10 to 20 ns pulse duration. A drawback of the eximer laser, however, is the energy density over the beam tends to have both large and small scale inhomogeneities. The application of the excimer laser for surgical procedures is described in U.S. Pat. No. 4,784,135, entitled "Far Ultraviolet Surgical and Dental Procedures," issued Nov. 15, 1988. For a historical background of the development and application of the eximer laser to ophthalmic surgery, see Chapter 1 of the Color Atlas/Text of Excimer Laser Surgery, ©1993 Igaku-Shoin Medical Publishers, Inc.

As early as 1983, researchers recognized the potential application of excimer laser light in reshaping the cornea. Since that time, a number of systems have been developed to reshape the cornea, using a variety of techniques such as variable sized circular apertures to correct for myopia, variable sized ring shaped apertures to correct for hyperopia, and variable sized slit shaped apertures to correct for astigmatism. These techniques collectively came to be known as photorefractive keratectomy. It has been recognized that using such apertures to correct for myopia, for example, a series of excimer laser shots using progressively smaller spot sizes could ablate away a portion of the cornea to effectively build a "corrective lens" into the cornea. These techniques are discussed, for example, in U.S. Pat. No. 4,973,330, entitled "Surgical Apparatus for Modifying the Curvature of the Eye Cornea," issued Nov. 27, 1990, and in U.S. Pat. No. 4,729,372, entitled "Apparatus for Performing Ophthalmic Laser Surgery," issued Mar. 8, 1988. Those skilled in the art of laser ophthalmological surgery have extensively developed the required exposure patterns using these variable size apertures to provide an appropriate amount of correction to various degrees of myopia, hyperopia, and astigmatism, and a combination of these conditions.

These multiple aperture systems, however, suffer a number of drawbacks. They tend to be complicated and inflexible, requiring a number of aperture wheels or masks and only providing standard forms of correction for myopia and hyperopia with circular symmetry and astigmatism with cylindrical symmetry. The human eye, however, tends to have more subtle defects. A system that could accommodate these defects and provide more adaptable solutions, as well as a physically simpler components, would thus be advantageous.

An apparatus for ablating tissue from the eye is shown in U.S. Pat. No. 4,973,330, referenced above. This apparatus includes an eximer laser, the laser beam of which impinges on the cornea, with the axis of the laser beam coinciding with the optical axis of the eye. Furthermore, a field stop limits the area of the laser spot on the cornea illuminated by the laser beam, and the size of this field stop is set in a temporarily variable manner according to the profile of the area to be removed so that the thickness of the area to be removed is a function of the distance from the optical axis of the eye.

The system described in U.S. Pat. No. 4,973,330 permits in this way setting the "laser energy deposited" on the cornea as the function of the distance from the optical axis of the eye, but only under the condition that the distribution of energy (i.e., the power of the laser beam spot) is homogeneous, or at least axially symmetrical. This, however, is a condition that excimer lasers in particular do not always fulfill. Inhomogeneous power distribution results in non-axially symmetrical removal. Moreover, the system described in U.S. Pat. No. 4,973,330 only permits the correction of spherical aberrations, not astigmatism.

An apparatus based on the same fundamental idea is known from U.S. Pat. No. 4,994,058, entitled "Surface Shaping Using Lasers", issued Feb. 19, 1991. That apparatus employs a "destructible field stop mask" instead of a field stop having a temporarily variable aperture.

Another class of apparatus for shaping the cornea by means of removing tissue is known from the various L'Esperance patents. These include U.S. Pat. No. 4,665,913, entitled "Method for Ophthalmological Surgery," issued May 19, 1987; U.S. Pat. No. 4,669,466, entitled "Method and Apparatus for Analysis and Correction of Abnormal Refractive Errors of the Eye," issued Jun. 2, 1987; U.S. Pat. No. 4,718,418, entitled "Apparatus for Ophthalmological surgery," issued Jan. 12, 1988; U.S. Pat. No. 4,721,379, entitled "Apparatus for Analysis and Correction of Abnormal Refractive Errors of the Eye," issued Jan. 26, 1988; U.S. Pat. No. 4,729,372, entitled "Apparatus for Performing Ophthalmic Laser Surgery," issued Mar. 8, 1988; U.S. Pat. No. 4,732,148, entitled "Method for Performing Ophthalmic Laser Surgery," issued Mar. 22, 1988; U.S. Pat. No. 4,770,172, entitled "Method of Laser-Sculpture of the Optically used Portion of the Cornea," issued Sep. 13, 1988; U.S. Pat. No. 4,773,414, entitled "Method of Laser-Sculpture of the optically used Portion of the Cornea," issued Sep. 27, 1988; and U.S. Pat. No. 4,798,204, entitled "Method of Laser-Sculpture of the Optically used Portion of the Cornea," issued Jan. 17, 1989. In that apparatus, a laser beam with a small focus spot is moved by a two-dimensional scanning system over the area to be removed. This apparatus, which operates as a "scanner," has the advantage that it can generate any two-dimensional profile of deposited energy "over the area to be removed." Because of the small size of the beam spot, the period of treatment, however, is very great, as power per area unit cannot be raised above a specific "critical" value.

Thus, current techniques do not adequately address the non-linear energy distribution of an excimer laser. The excimer laser includes both large scale and small scale non-linearities in its energy distribution. This can cause over-ablation and under-ablation of certain areas of the eye under treatment. Thus it would be desirable to provide a system that further homogenizes the effective energy deposited on the eye.

Systems that use apertures to create a series of progressively smaller shot sizes also suffer from the disadvantage of creating sharp ridges in the treatment zone of the cornea. Especially near the periphery of the treatment zone, a number of shots are typically required to create the necessary ablation depth at each particular spot size. The typical ablation depth for each shot is 0.2 $\mu$m. When multiple shots are required at a single aperture size, the ridge depth reinforces, creating an effective ridge of some multiple of 0.2 $\mu$m. For example, five shots would result in a ridge height of 1.0 $\mu$m. These sharp ridges in the treatment zone can lead to unwanted epithelial regrowth, especially when correcting high diopter defects. A system that minimizes such ridges would promote smoother epithelial healing, preventing excessive regrowth and allowing the corrected eye to retain its correction for a longer period of time and with more stability.

Before ablating, most current excimer techniques also require physically scraping away the epithelial layer from the eye. This can be a traumatic procedure for the patient, and requires a high degree of precision by the surgeon. Alternative, less invasive methods of removal of the epithelium before ablation of the cornea are thus desirable.

SUMMARY OF THE INVENTION

The method and apparatus according to the invention provides corneal correction using laser "polishing" or "dithering" in which subsequent shots used to ablate the eye are randomly or otherwise moved from a center axis of treatment to prevent the formation of large ridges in the treatment zone.

Further according to the invention, instead of using various aperture shapes, a relatively large beam is moved along the line of hyperopic or astigmatic correction desired, creating a line of overlapping shots. If further correction is necessary, overlapping lines are then created using various beam sizes, thus forming the desired correction curve in the cornea.

Further according to the invention, using this scanning beam technique, various non-symmetrical optical defects are corrected, such as a "curved" astigmatism, by modifying the line of travel of the overlapping shots or by otherwise generating a sequence of shots to appropriately ablate a non-symmetrical defect.

Further in the system and method according to the invention, the epithelium is removed using laser ablation. The epithelium is first dyed with an infrared fluorescent dye. The epithelium is then continually ablated using a beam covering the area of epithelium to be removed until an infrared scanning device recognizes that some portion of the epithelium is gone, as indicated by a lack of fluorescence. Then, either manually or under computer control, the spot size is reduced and areas that still fluoresce are ablated until they no longer fluoresce. This is repeated until the epithelium has been removed from the entire treatment area. This technique can also map the initial thickness of the epithelium before removal.

BRIEF DESCRIPTION OF THE DRAWINGS

A better understanding of the present invention can be obtained when the following detailed description of the preferred embodiment is considered in conjunction with the following drawings, in which:

FIGS. 4A and 4B are illustrations showing a shot pattern for astigmatic correction according to the invention;

FIG. 5 is an illustration of a treatment zone illustrating a shot treatment pattern for a curved astigmatism according to the invention;

FIGS. 6A and 6B are illustrations showing a shot pattern for treatment of hyperopia according to the invention;

DETAILED DESCRIPTION OF THE PREFERRED EMBODIMENT

Figure 1A:
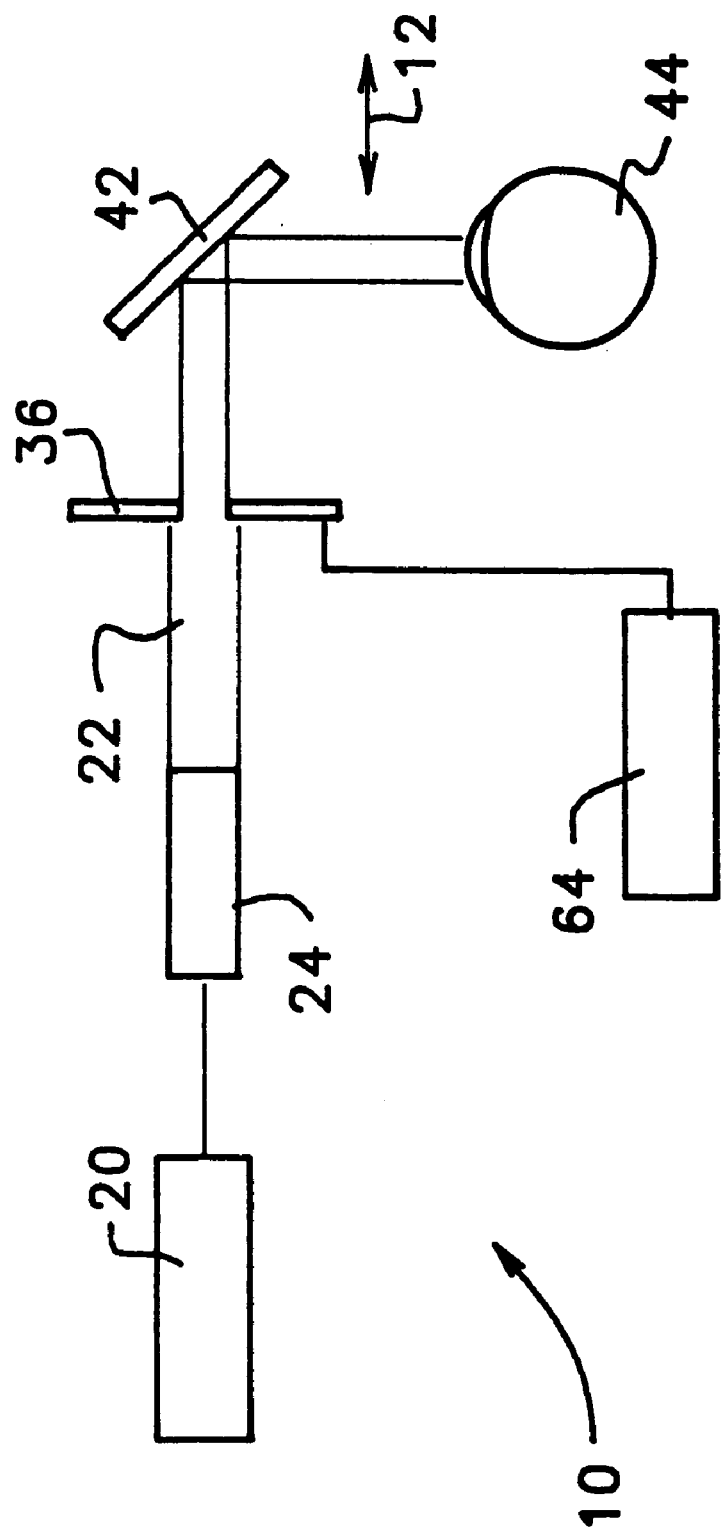
FIG. 1A is a simplified diagram illustrating a typical excimer laser eye surgery system in which can be implemented the apparatus and method according to the invention.

FIG. 1A, according to the invention, shows an excimer laser 20 providing a beam to a beam homogenizer 24 that also includes focusing components. The beam homogenizer 24 then provides a relatively homogeneous beam 22 to a field stop in the form of a diaphragm 36, which is regulated by a control unit 64 in such a manner that it limits the laser spot on an eye 44 to an area the maximum size of which is between approximately 10% and approximately 90% of the area of the region in which the tissue is to be removed when ablation is performed to correct for astigmatism or hyperopia. This preferred maximum size is more dependent on the shape and size of the area to be ablated rather than any fixed percentage, and could be, for example, between 20% and 80%. The larger the size of the spot that can be used the better, as that reduces treatment time.

Moreover, a beam manipulator unit in the form of a scanning mirror 42 is provided that also is regulated by the control unit 64. The scanning mirror 42 moves the axis of the beam 22 over at least a part of the region on the eye 44 in which the tissue is to be removed.

The invention thus provides an eye surgery system 10 for shaping the cornea by removing tissue with which removal of non-axially symmetrical profiles can be realized in a relatively shorter time. Further, the eye surgery system 10 compensates for any inhomogeneous distribution of energy over the beam spot.

By this means, not only can a very small spot be illuminated, as in the case of a scanning unit, but also a relatively large region can be illuminated so that the treatment can occur relatively quickly. To shorten treatment time, it is preferred to maintain the size of the laser spot on the eye 44 as large as possible for as long as possible, for example to at least 50% of the size of the region to be treated.

The scanning mirror 42 can, by way of illustration, tilt about or around at least one axis. Mirror elements that can be used, and in particular that can be tilted about two axes, are described in U.S. Pat. No. 4,175,832, for example.

Further, the control unit 64 can regulate the size of the laser spot on the eye 44 in correlation to the movement of the beam axis (through use of the scanning mirror 42) on the eye 44, thus precisely regulating the energy deposited on a specific area of the eye 44. Thus, non-axially symmetrical profiles can be generated on the corneal surface of the eye 44. Different types of diaphragms 36 can be used, for example ovals or circles with blocked centers.

Moreover, the scanning mirror 42 can be placed in the beam 22 not only after the diaphragm 36, but also before the diaphragm 36. It would then be preferable to move the diaphragm 36 synchronously with the scanning mirror 42.

In correcting spherical aberrations, the control unit 64 preferably moves the scanning mirror 42 such that the beam 22 oscillates from shot to shot in at least one direction, such as is illustrated by an arrow 12. Such oscillation compensates for inhomogeneity of the energy distribution over the beam 22. This oscillation finds application regardless of the maximum beam size.

To correct astigmatism, the scanning mirror 42 moves the axis of the beam 22 between at least two directions, neither of which are collinear with the axis of treatment of the eye 44. This permits treating an astigmatic eye, which, without being limited by theory, the latest research states has not one apex, but two. That is, it has the shape of camel humps. Also, the control unit 64 regulates the scanning mirror 42 such that the axis of the beam 22 oscillates at least one-dimensionally about each direction, thus compensating for homogeneity of the beam 22.

To correct for hyperopia, the axis of the beam 22 is preferably moved on a conic-shaped shell surface, it also being possible to superimpose an at least one-dimensional oscillation to compensate for inhomogeneity of the beam 22. By moving on a conic-shaped shell surface, a circular pattern of overlapping shots is projected onto the eye 44.

In adapting the diaphragm 36 to the typical shape of the cross-section of excimer laser beams, the diaphragm 36 may also have a non-axially symmetrical shape, with the diaphragm 36 being turned in order to homogenize the deposited energy during the movement of the axis of the beam 22 on the conic shell. The homogenization is enhanced if the turning of the diaphragm 36 occurs asynchronously to the rotation of the axis of the beam 22 on the conic shell.

Figure 1B:
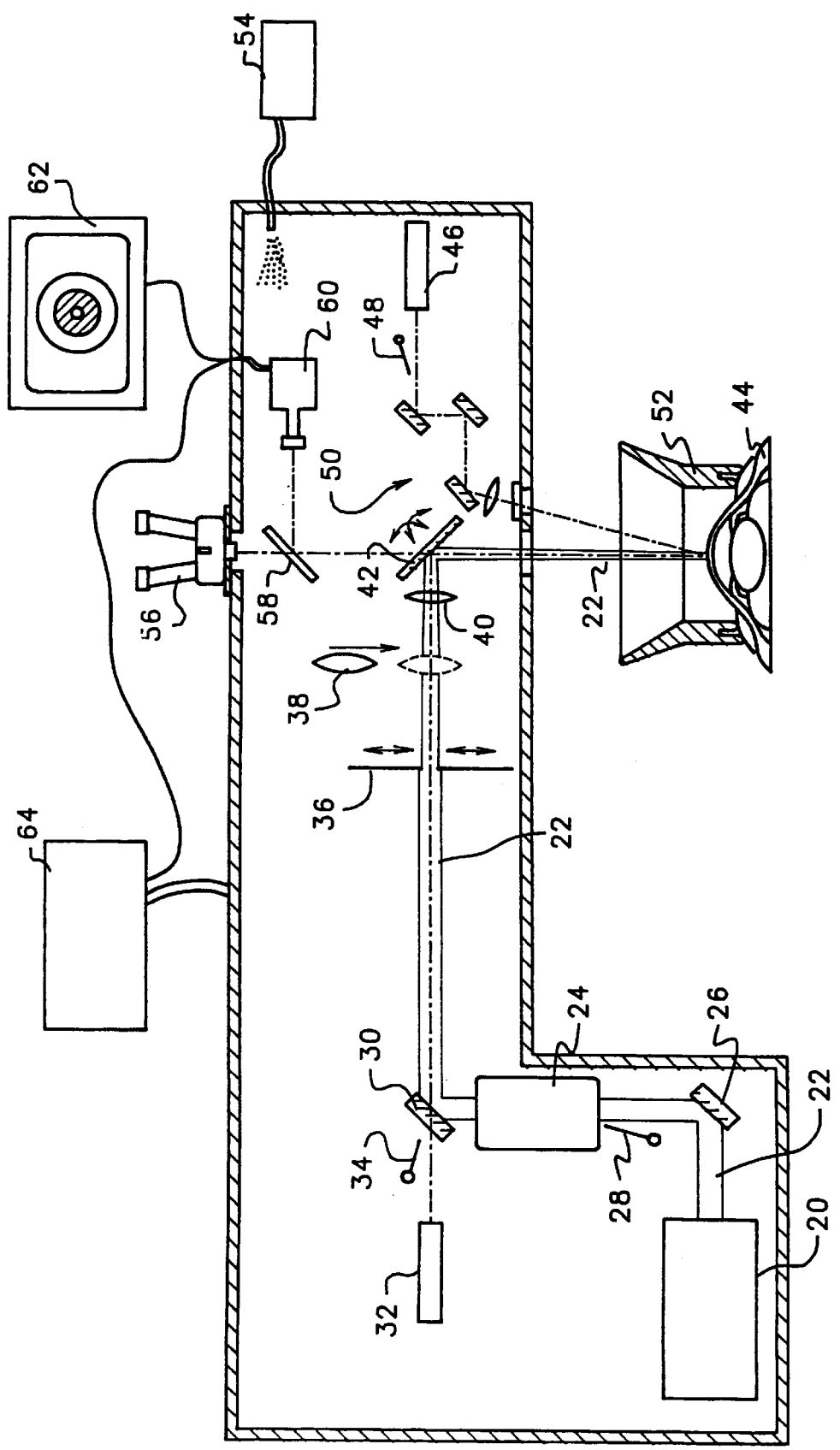
FIG. 1B is a more detailed diagram illustrating the system of FIG. 1A.
Figures 1C, 1D:
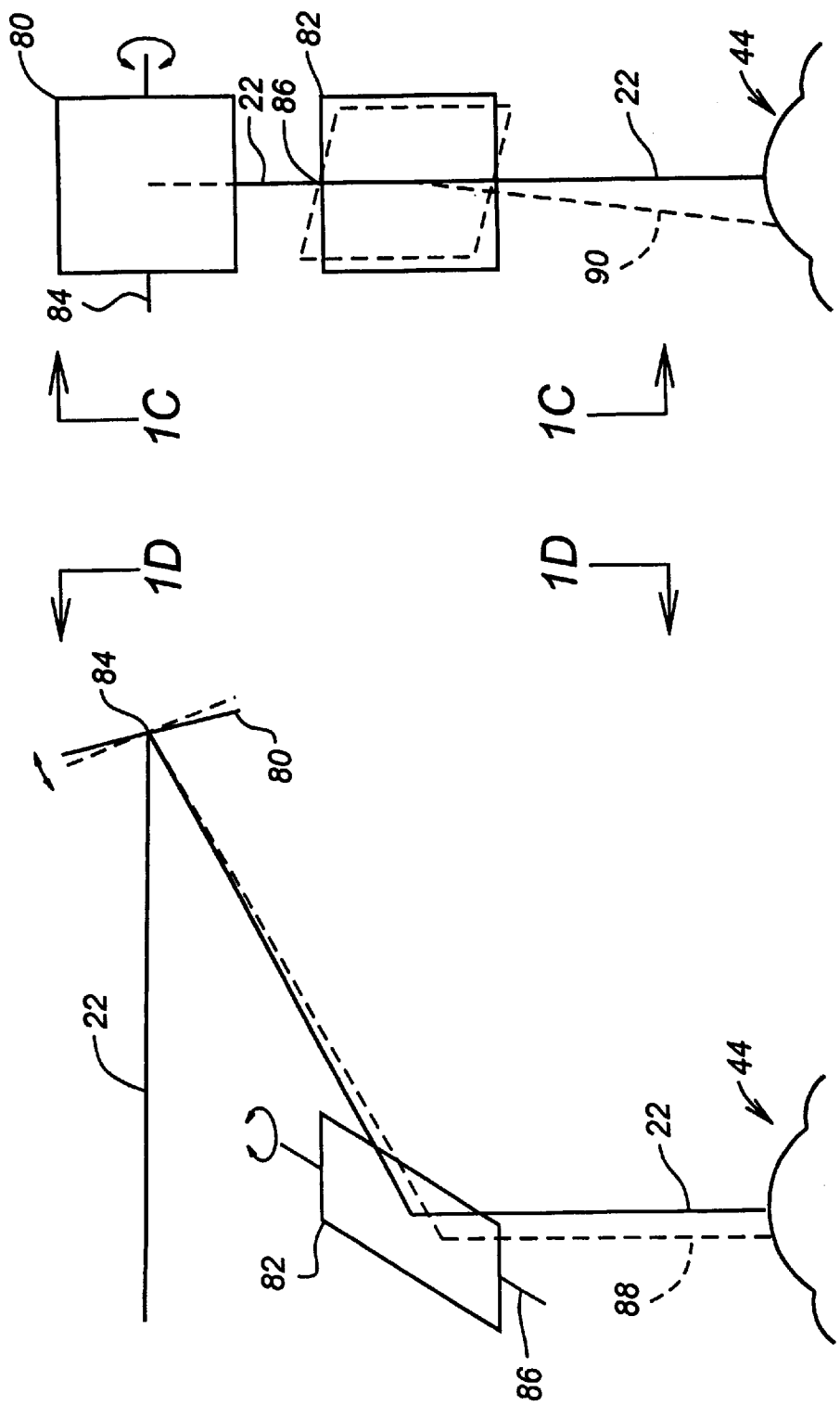

FIG. 1B shows additional details of the typical eye surgery system 10 in which the method and apparatus according to the invention would be implemented. An excimer laser 20 provides a pulsed beam 22 to a beam homogenizer 24 after reflection from optics 26. A shutter 28 is also provided to block transmission of the pulsed beam 22 to the beam homogenizer 24. The excimer laser 20 is a typical excimer laser as is well known in the art. It preferably provides a 193 nm wavelength beam with a maximum pulse energy of 400 mJ/pulse. The excimer laser 20 preferably provides maximum power at the treatment site of 1 W, with a pulse frequency of 10 Hz and a pulse length of 18 ns. Of course a variety of other excimer lasers could be used, and the apparatus and method according to the invention further have application where a laser other than an excimer laser is used. By way of example, the wavelength of the light from the laser is preferably less than 400 nm, as that provides the desired ablating action with reduced thermal heating. Further, other pulse energies can be provided, such as all the way down to 200 mJ/pulse, with typical repetition rates of 60 to 100 pulses per second with a typical pulse length of 10 to 30 ns. Again, all of these are merely typical values, and deviation from them can be made without changing the spirit of the apparatus and method according to the invention. Further examples of such laser systems can be found in U.S.

Pat. No. 4,665,913, entitled "Method for Ophthalmological Surgery," issued May 19, 1987, and U.S. Pat. No. 4,729,372, entitled "Apparatus for Performing Ophthalmic Laser Surgery," issued Mar. 8, 1988.

The beam homogenizer 24 preferably includes standard homogenization and focusing hardware, which can be based both on optical mixing of the beam and on rotation of the beam. For an example of typical beam homogenization hardware, see U.S. Pat. No. 4,911,711 entitled, "Sculpture Apparatus For Correcting Curvature Of The Cornea," issued Mar. 27, 1990. Note that by providing the "dithering" according to the invention as discussed below, the beam homogenizer 24 can be simpler than the beam homogenization hardware shown in that reference. From the beam homogenizer 24, the pulsed beam 22 is then reflected off of optics 30, which also passes a red pilot laser beam from a pilot laser 32. This pilot laser 32 is preferably a 633 nm helium neon laser of less than 1 mW of power. The red pilot beam from the pilot laser 32 can also be blocked by a shutter 34. The pilot laser 32 is aligned so that its optical pathway coincides with the pulsed beam 22. The pilot laser 32 provides the functions of centering the beam 22 on the axis of treatment of the eye 44, and also provides for focusing on the eye 44, as is discussed below. Further, it can provide an optical fixation point for the patient, although a different laser or light source could also be provided for that purpose.

From the optics 30, the pulsed beam 20 (now also co-aligned with the beam from the pilot laser 32) then passes through an adjustable diaphragm 36, which allows the beam size to be adjusted before it enters the final optics. After the diaphragm 36, a spot mode lens 38, when in place, provides further concentration of the beam 22, allowing spot ablation of certain defects in the eye by a physician performing therapeutic rather than refractive surgery. The spot mode lens 38 is thus moved into and out of place depending on whether therapeutic or refractive treatment is desired.

Following the spot mode lens 38, a focusing lens 40 directs the beam 22 onto the scanning mirror 42, which then reflects the beam 22 onto a patient's eye 44. Note that the portion of the beam 22 from the pilot laser 32 is used for both adjusting the distance of the eye 44 from the entire eye surgery system 10 and for providing centering, as will be discussed below. The focusing lens 40 focuses light such that when the eye 44 is at the optimal distance, the beam 22 is properly focused onto the eye 44.

These various lenses and mirrors thus combine to form an optical system providing an excimer beam to the cornea. The optical system creates a laser spot on the cornea, and the spot size is adjustable, along with its location. It will be readily appreciated that a wide variety of different systems could be used to optically provide such a beam. For example, a lens could be used to adjust the spot size rather than an aperture, and instead of a scanning mirror, the patient or the patient's eye 44 could be physically moved to provide for shots at different locations on the eye 44.

Also provided in the system according to the invention is a focusing laser 46, whose beam can also be blocked by a shutter 48. The focusing laser 46 is preferably a green helium neon laser providing a beam of a wavelength of 535 nm and less than 1 mW of power. The beam from the focusing laser 46 travels through optics 50 and impinges on the eye 44 at an angle. The distance of the eye 44 from the eye surgery system 10 is adjusted such that both the beam from the pilot laser 32 and the beam from the focusing laser 46 impinge on the surface of the eye 44 at the same point.

Further provided is an optional fixation mask 52, which is well known in the art and is used to stabilize the eye 44 during surgery. It can include debris removal components, and is typically attached to the eye 44 through either a vacuum suction ring or through hooks. A clean gas purge unit 54 ensures that the optics and the beams in the system are free from any floating debris.

A microscope 56 is provided for the physician to observe progress during ablation of the surface of the eye 44. The microscope 56 is preferably a ZEISS OPMI "PLUS" part No. 3033119910, with magnifications of 3.4, 5.6 and 9.0 times. Field illumination is provided by a cold light source not shown, which is preferably the Schott KL1500 Electronic, ZEISS part number 417075. This microscope 56 focuses through the scanning mirror 42 and also focuses through a splitting mirror 58. The splitting mirror further provides a view of the eye 44 to an infrared video unit 60, which is used for the epithelial ablation discussed below. The infrared video unit 60 preferably provides an image output to a capturing video screen 62 and to a control unit 64. The infrared video unit 60 is preferably sensitive to both infrared light and visible light.

The control unit 64, which is typically a high performance computer compatible with an IBM PC by International Business Machines Corp., further preferably controls all components of the eye surgery system 10, including the shutters 28, 34, and 48, the diaphragm 36, the spot mode lens 38, and the scanning mirror 42.

Figure 2A:
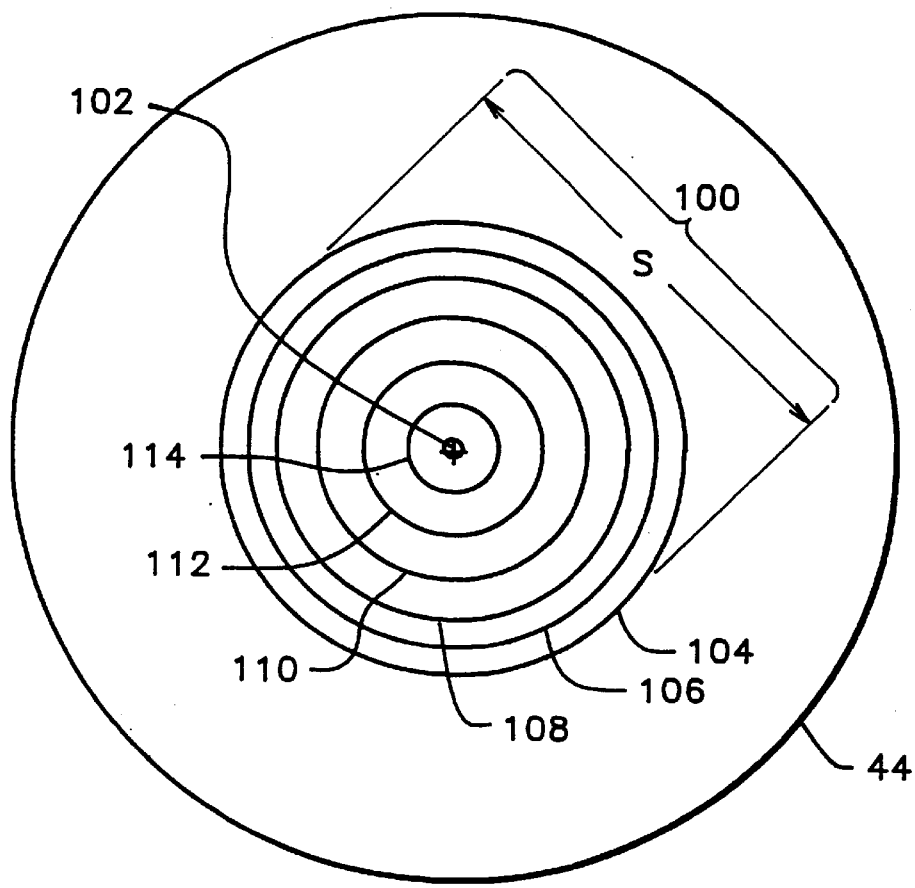
FIG. 2A is a view along the center axis of the treatment zone illustrating a typical large beam ablation pattern to correct for myopia.

FIG. 2A shows a simplified top view of the cornea of a typical eye 44 on which myopic correction has been performed. A treatment zone 100 of a width S is centered on an axis of treatment 102, which does not necessarily correspond to the optical axis of the eye 44. The treatment zone 100 is bounded by a first outer ablation ring 104, with subsequent ablation rings 106 to 114 shown spaced more widely towards the center of the axis of treatment 102 (note that preferably the smaller shots are performed first).

This wider spacing is topographical in effect, as in a typical system, the change in spot radius between shots may actually be constant, but with a greater number of shots performed toward the periphery of the treatment zone 100. Although only six ablation zones are shown, in a typical ablation pattern a greater number of spot sizes are used, and a greater number of shots are also performed. The ablation function for calculating the necessary depth of ablation for myopia is discussed below in conjunction with FIG. 7A.

Figure 2B:
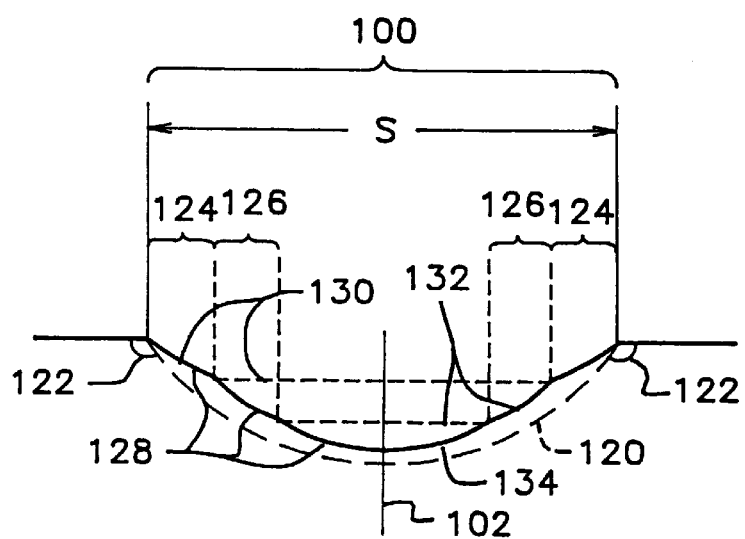
FIG. 2B is a side profile of FIG. 2A, further illustrating the use of transition zones.

In performing high dioptric correction for myopia, using the standard ablation function discussed below may result in an excessive depth of ablation along the axis of treatment 102. As illustrated in FIG. 2B, the standard equation for myopic ablation would result, for example, in a curve 120 which would lead to a high depth of ablation along the axis of treatment 102, and would also result in sharp edges 122 at the corner of the treatment zone 100. For simplicity, FIG. 2B shows the effect of treatment on a flat surface rather than the surface of the cornea. For such a high degree of correction, the use of transition zones can significantly reduce the edge effects in healing and can also reduce the center depth of ablation along the axis of treatment 102. These transition zones 124 and 126 effectively create a multi-focal lens. In FIG. 2B, two transition zones 124 and 126 are shown resulting in a shallower ablation curve 128. The first of these transition zones 124 is created by performing a myopic ablation over the full width S of the treatment zone 100 using a lesser degree of correction than the ultimate correction desired. Only those shots of a radius falling into the radius of the transition zone 124 are performed, however, thus leaving a uniformly ablated surface inside transition zone 124 for further treatment. This results in an initial curve 130.

Then, another series of myopic ablation shots using the myopic ablation function discussed below is performed using a somewhat greater degree of correction but using a smaller "treatment zone" (in actual practice, the smaller shots are preferably performed first). This resulting curve and uniformly ablated area 132 creates the second transition zone 126. Finally, a series of shots are performed for the full desired correction but using an again narrower zone of treatment, resulting in the final curve 134. The use of transition zones is known to the art of photorefractive keratectomy, and is described, for example, in Chapter 6 of the Color Atlas/Text of Excimer Laser Surgery, © 1993 Igaku-Shoin Medical Publishers, Inc. These transition zones 124 and 126 reduce any sharp edges 122 from being created, which could otherwise result in undesirable patterns of epithelia regrowth, and also reduce ultimate depth of ablation along the axis of treatment 102.

The following are two typical tables showing transition zones. For treatment to correct -9.00 diopters of myopia over a 5 mm treatment zone 100, the following transition zones could be used:

| No. | Min. [mm] Max. [mm] | Correction [diopters] |
| --- | --- | --- |
| 1 | 0.50–4.00 | -9.00 |
| 2 | 4.00–4.20 | -7.50 |
| 3 | 4.20–4.40 | -6.00 |
| 4 | 4.40–4.60 | -4.50 |
| 5 | 4.60–4.80 | -3.00 |
| 6 | 4.80–5.00 | -1.50 |

Using this table, first a standard myopic correction using the equation discussed below would be performed for the desired -9.00 diopters of correction, but instead over a treatment zone 4.00 mm wide. This provides full correction in the middle 4.00 mm zone. Then, a transition is created by ablating from 4.00 to 4.20 mm using the lesser correction of -7.50 diopters. This is repeated for the subsequent entries in the table, thus forming transition zones of a greater radius of curvature.

Without the transition zones, 88 μm would be ablated at the axis of treatment 102; with the transition zones, only 71 μm is ablated—20% less. This is good for the stability of the cornea.

An example of treatment for -12.00 diopters over a full 7 mm treatment zone 100 is illustrated below:

| No. | Min. [mm] Max. [mm] | Correction [diopters] |
| --- | --- | --- |
| 1 | 0.50–2.00 | -12.00 |
| 2 | 2.00–2.20 | -11.54 |
| 3 | 2.20–2.40 | -11.08 |
| 4 | 2.40–2.60 | -10.62 |
| 5 | 2.60–2.80 | -10.15 |
| 6 | 2.80–3.00 | -9.69 |
| 7 | 3.00–3.20 | -9.23 |
| 8 | 3.20–3.40 | -8.77 |
| 9 | 3.40–3.60 | -8.31 |
| 10 | 3.60–3.80 | -7.85 |
| 11 | 3.80–4.00 | -7.38 |
| 12 | 4.00–4.20 | -6.92 |
| 13 | 4.20–4.40 | -6.46 |
| 14 | 4.40–4.60 | -6.00 |
| 15 | 4.60–4.80 | -5.54 |
| 16 | 4.80–5.00 | -5.08 |
| 17 | 5.00–5.20 | -4.62 |
| 18 | 5.20–5.40 | -4.15 |
| 19 | 5.40–5.60 | -3.69 |
| 20 | 5.60–5.80 | -3.23 |
| 21 | 5.80–6.00 | -2.77 |
| 22 | 6.00–6.20 | -2.31 |
| 23 | 6.20–6.40 | -1.85 |
| 24 | 6.40–6.60 | -1.38 |
| 25 | 6.60–6.80 | -0.92 |
| 26 | 6.80–7.00 | -0.46 |

Figure 3A:
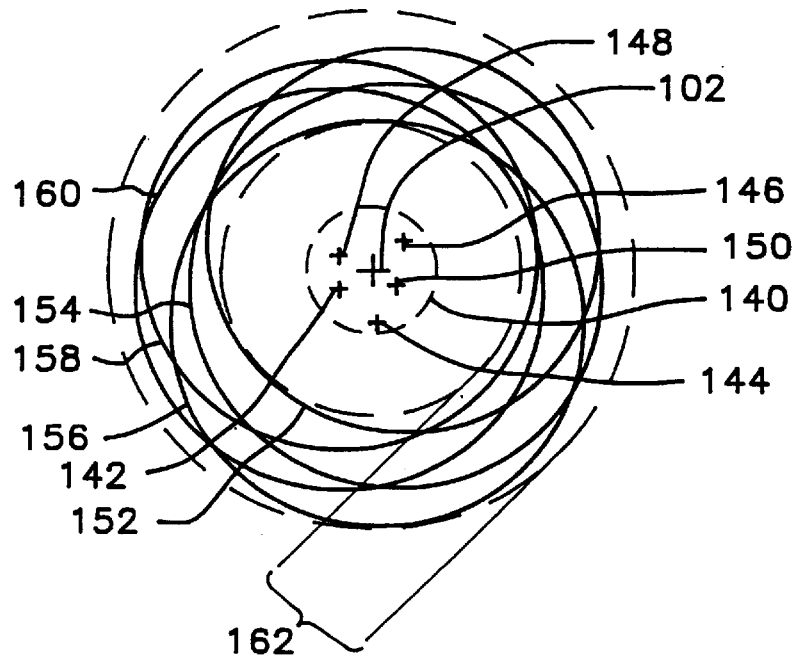
FIG. 3A is a view along the center axis of the treatment zone illustrating random dithering according to the invention.
Figure 3B:
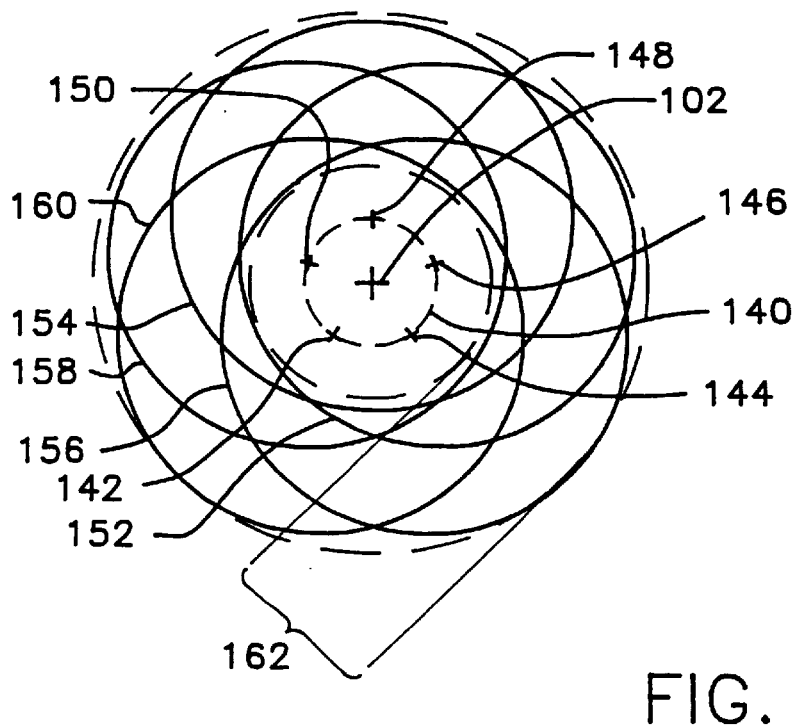
FIG. 3B is a view along the center axis of the treatment zone illustrating circular dithering according to the invention.

FIGS. 3A and 3B show an ablation pattern corresponding to one of the ablation rings 104 to 114 of FIG. 2A, but using the laser "dithering," or "polishing," according to the invention. The term "dithering" is used in the sense that small random or pseudo random fluctuations are added to the beam 22 to "smooth" particular errors that would otherwise build up. Assuming one of the ablation rings 104 to 114 of FIG. 2A includes five shots at a particular spot size, FIGS. 3A and 3B show the effect achieved according to the method and apparatus of the invention. In FIG. 3A, the axis of treatment 102 is shown, upon which shots in past systems have been centered, as shown in FIG. 2A.

According to the invention, however, the centers of the five shots are randomly distributed in a dithering zone 140 with the center axis of each shot being away from the axis of treatment 102. Five shots using randomly distributed centers 142 through 150 result in five individual excimer laser ablation shots 152 through 160. The radius of the dithering zone 140 is preferably somewhat less than the radius of the shots themselves. As can be seen, any reinforcement—i.e., ridge height greater than a single shot ridge height—occurs only incidentally, and generally the ridges are distributed over a dithering band 162. This provides a "smoothing" effect, reducing average ridge height.

FIG. 3B shows an alternative manner of performing this polishing, in which the shot centers 142 through 150 are evenly distributed around the periphery of the dithering zone 140. This case insures that none of the ablation shots 152 through 160, even though of the same radius, form reinforcing ridges.

In this manner, a smoother surface of the eye 44 is achieved during ablation to correct for myopia. This polishing, or dithering, could also be described as an "oscillation" of the laser spot upon the cornea. This dithering could also be one dimensional rather than two, and could also be created by vibrating the patient's eye 44, such as by vibrating the mask 52 or the patient himself. For example, a small mechanical vibrator could be placed in a patient table or in the mask 52. This could then provide the oscillation necessary. As can be readily appreciated, such a dithering technique can be applied to other forms of correction, such as using ring apertures and slit apertures to correct for hyperopia and astigmatism, as are known in the art. Further, the dithering could be applied to any other shot patterns such as for hyperopia and astigmatism, thus reducing the effects of both ridge height and beam 22 inhomogeneity.

FIG. 4 illustrates a large beam scanning pattern used to correct for astigmatism according to the system and method of the invention. In the prior art, variable size slits were generally used to perform this correction, requiring further hardware and generally inflexible patterns of correction.

The method and apparatus according to the invention, however, correct astigmatism within the treatment zone 100, here with width S and length L, through a series of lines 170 and 172 created by a series of overlapping shots in the area to be corrected for astigmatism. In the diagram, only the first line 170 and the second line 172 are shown, with the first line created using smaller spot sizes than the second line 172. According to the method of the invention, a lesser or greater number of lines are used to provide the desired degree of correction for astigmatism. This results in the ablation profile as shown in FIG. 4B. This profile generally corresponds to the curvature needed for a myopia ablation, whose formula is discussed below in conjunction with FIG. 7A.

A typical pattern used for ablating to correct for astigmatism for a −2.00 diopter correction would involve shots of:

| No. | Spot Size | Shots |
|-----|-----------|-------|
| 1   | 1.067     | 11    |
| 2   | 1.679     | 8     |
| 3   | 2.141     | 7     |
| 4   | 2.484     | 7     |
| 5   | 2.726     | 6     |
| 6   | 2.885     | 6     |
| 7   | 2.977     | 6     |
| 8   | 3.019     | 6     |
| 9   | 3.022     | 6     |
| 10  | 3.000     | 6     |

At each spot size, a line is created corresponding to the lines 102 and 104, and preferably the spots overlap by approximately 88%. This would create an appropriate modified curvature corresponding to a −2.00 diopter correction for astigmatism. These would be spread over a 3 mm width S of the treatment zone 100.

FIG. 5 is an illustration of shot patterns used to correct for non-symmetrical astigmatism. In this case, only a single treatment line 174 is shown; typically, a greater number of lines would be used, but for clarity, the single line 174 illustrates the treatment of a curved astigmatism that does not extend linearly across an axis of treatment 102 of the eye 44. In this way, a greater variety of types of astigmatism are correctable.

FIG. 6A illustrates the large beam scanning according to the invention used to correct for hyperopia without using ring apertures. Instead, only the single diaphragm 36 is used to adjust the spot size, and a circular ablation ring 180 over the treatment zone 100, as is well known to those skilled in performing hyperopic ablation, is created using multiple rings of different spot sizes and various overlaps. The approximate ablation profile is shown in FIG. 6B. The formula for the curvature for hyperopic ablation is discussed below in conjunction with FIG. 7B.

It will be noted that the shots for hyperopic ablation extend beyond the zone of treatment 100 of width S. The shots outside of this area do not provide for optical correction, but instead provide a smooth transition at the edge of hyperopic ablation. Further, although the circular ablation ring 180 is not shown extending all the way to the center of the axis of treatment 102, the final series of shots at the largest shot size preferably extend very close to that axis, to provide a smooth profile from the center of the axis of treatment 102 to the edge of the treatment zone 100.

A typical shot pattern for hyperopic correction of 5.00 diopters would involve shots of:

| No. | Spot Size | Shots | Overlap |
|-----|-----------|-------|---------|
| 1   | 2.000     | 1052  | 99.25[%] |
| 2   | 2.469     | 128   | 95      |
| 3   | 3.060     | 104   | 95      |
| 4   | 3.966     | 80    | 95      |
| 5   | 4.600     | 27    | 87      |

In this pattern, each series of shots is used to create a ring with centers at a radius of 2.5 mm from the axis of treatment 102 of the eye 44. In this case, the preferred overlap is variable per treatment ring, and is illustrated in the table.

As can further be appreciated, although the illustrated shot patterns use circular apertures, another aperture shape could be used to create the hyperopic correction pattern and the astigmatism correction pattern according to the invention. For example, an oval shot shape could be used, and that oval could be rotated during the hyperopic correction, such that one axis of the oval pointed to the axis of treatment 102 of the eye 44. Alternatively, the oval could be rotated asynchronously with the rotation about the axis of treatment 102, thus further reducing the effects of inhomogeneity of the beam 22.

Figure 7A:
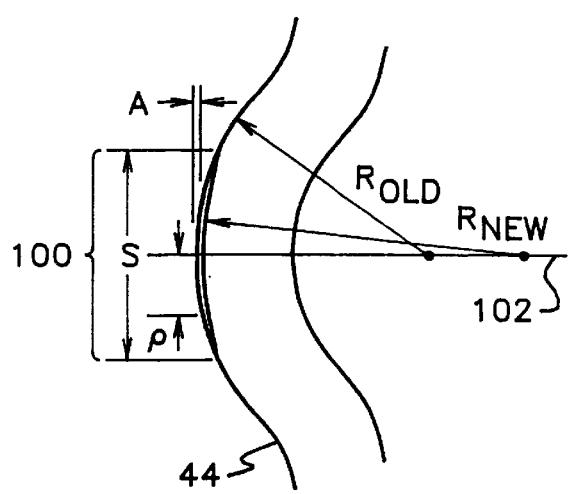
FIGS. 7A and 7B are side profiles of the cornea illustrating initial and ending radii of curvature over a treatment zone for correction of myopia and hyperopia.
Figure 7B:
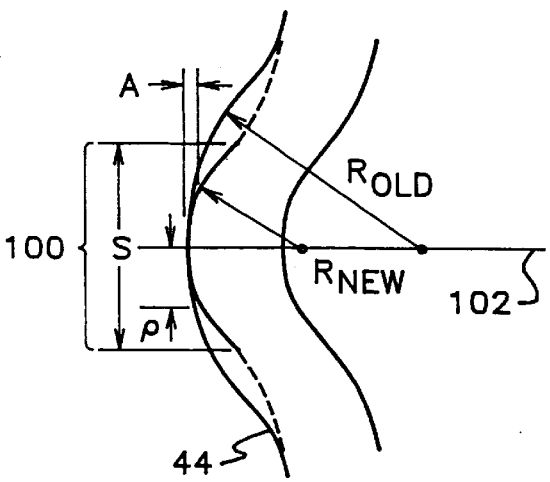

FIGS. 7A and 7B illustrate various mathematical attributes of the ablation profiles of the preceding ablation patterns. FIG. 7A shows a typical ablation profile for myopic ablation and FIG. 7B illustrates a typical ablation profile for hyperopic ablation. In both, the initial radius of the cornea of the eye 44 is given by $R_{OLD}$ and the new, desired radius of the cornea of the eye 44 is given by $R_{NEW}$. The absolute zone of treatment 100 is designated as a width S, which corresponds to the effective area that performs the corrective function. It is typically between 2 and 8 mm, but can be larger or smaller. The depth of ablation at any point within the treatment zone 100 of width S is given by a variable A, which stands for ablation depth. The distance from the axis of treatment 102 is given by a variable $\rho$.

To calculate the new radius $R_{NEW}$, the old radius $R_{OLD}$ and a desired dioptric correction $D_{CORR}$ is used in the following equation:

$$\text{NEW\_RADIUS}(R_{old}, D_{CORR}) = \frac{n-1}{\frac{n-1}{R_{OLD}} + D_{CORR}}$$

NEW_RADIUS returns a parameter indicating the new radius of correction needed, $R_{NEW}$, for a given $R_{OLD}$ and $D_{CORR}$. Both $R_{OLD}$ and $R_{NEW}$ are measured in meters, and are typically between 5 and 15 mm.

The formula for calculating the necessary depth of ablation to correct for myopia as illustrated in FIG. 7A is given below:

$$\text{MYO\_ABLATE}(\rho, R_{OLD}, S, D_{CORR}) =$$

$$\sqrt{R_{OLD}^2 - \rho^2} - \sqrt{\left(\frac{R_{OLD}(n-1)}{n-1+R_{OLD}D_{CORR}}\right)^2 - \rho^2} -$$

$$\sqrt{R_{OLD}^2 - \frac{S^2}{4}} + \sqrt{\left(\frac{R_{OLD}(n-1)}{n-1+R_{OLD}D_{CORR}}\right)^2 - \frac{S^2}{4}}$$

The myopic ablation function MYO_ABLATE returns a needed depth of ablation at a particular distance $\rho$ from the axis of treatment 102, given the uncorrected radius of curvature of the eye 44 $R_{OLD}$, a desired zone of correction S, and a desired degree of correction $D_{CORR}$. The function MYO_ABLATE also provides the appropriate degree of correction across the width S of a trench used to correct for astigmatism, as illustrated in FIGS. 4A and 4B.

Turning to FIG. 7B, the formula for hyperopic ablation is given below:

$$\text{HYP\_ABLATE}(\rho, R_{OLD}, D_{CORR}) = \sqrt{R_{OLD}^2 - \rho^2} - \sqrt{\left(\frac{R_{OLD}(n-1)}{n-1+R_{OLD}D_{CORR}}\right)^2 - \rho^2} + \frac{R_{OLD}(n-1)}{n-1+R_{OLD}D_{CORR}} - R_{01}$$

The hyperopia ablate function HYP_ABLATE only uses three parameters, as it does not need optical zone of correction S.

These specific algorithms for creating appropriate curvatures are well known in the art and can be found in MUNNERLYN, C. AND KOONS, S., PHOTOREFRACTIVE KERATCTOMY: A TECHNIQUE FOR LASER REFRACTIVE SURGERY, Cataract Refract Surg., Vol. 14, (January 1988).

Further, in the routines for performing ablation discussed below in conjunction with FIGS. 9–14, the inverse of these equations are needed. While the above equations return a depth of ablation needed at a particular value of $\rho$ for a given degree of correction, the inverse equations do the exact opposite. They return the particular value of $\rho$ at which a particular depth of ablation is needed given a particular degree of correction. These equations are given below:

$$\text{INV\_MYO\_ABLATE}(R_{OLD}, S, A, D_{CORR}) =$$

$$2(R_{OLD}^2 + R_{NEW}^2) - (C-A)^2 - \left(\frac{R_{OLD}^2 - R_{NEW}^2}{C-A}\right)^2 \text{ where } C =$$

$$\sqrt{R_{NEW}^2 - (S/2)^2} - \sqrt{R_{OLD}^2 - (S/2)^2} \text{ and } R_{NEW} =$$

$$\text{NEW\_RADIUS}(R_{OLD}, D_{CORR})$$

$$\text{INV\_HYP\_ABLATE}(R_{OLD}, A, D_{CORR}) =$$

$$2(R_{OLD}^2 + R_{NEW}^2) - (C-A)^2 - \left(\frac{R_{OLD}^2 - R_{NEW}^2}{C-A}\right)^2 \text{ where } C =$$

$$R_{NEW} - R_{OLD} \text{ and } R_{NEW} = \text{NEW\_RADIUS}(R_{OLD}, D_{CORR})$$

The inverse myopic ablation function INV_MYO_ABLATE returns a parameter indicating the distance corresponding to $\rho$ from the center of ablation in meters given a depth of ablation A, also in meters. It also uses the parameters $R_{OLD}$, S, and The inverse hyperopic ablation function INV_HYP_ABLATE also returns a radius from the center of ablation in meters corresponding to $\rho$, given a depth of ablation A at a certain correction $D_{CORR}$. It returns $\rho$ indicating how far away from the center of ablation a certain depth of ablation will be found.

Figure 8:
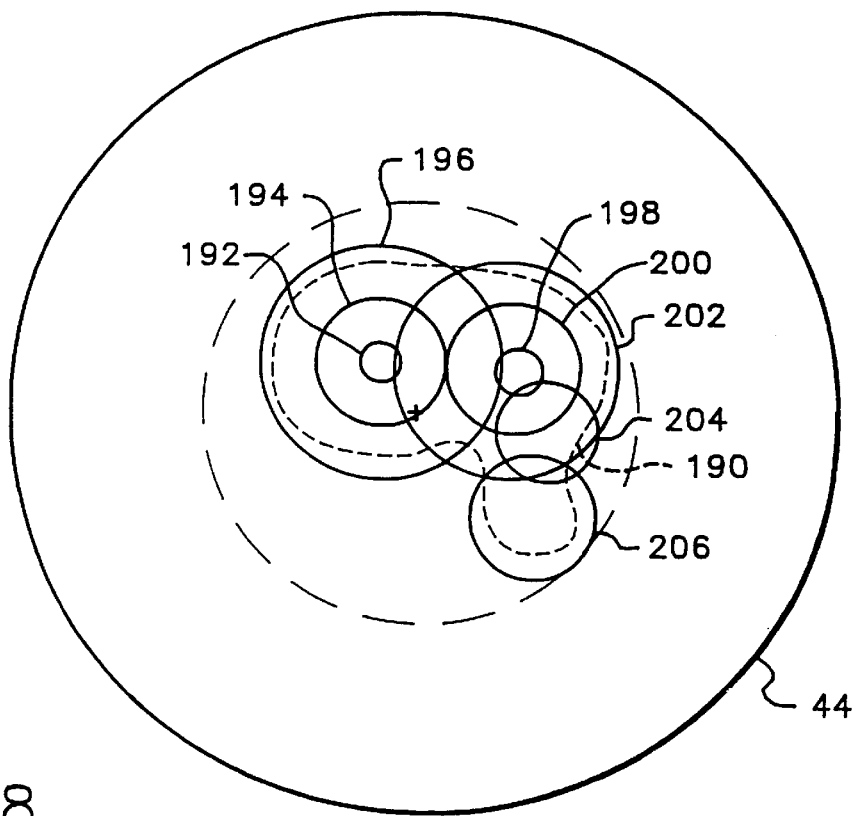
FIG. 8 is an illustration of shot patterns used to correct for general non-symmetrical aberrations of the eye according to the invention.

FIG. 8 illustrates how the system using aiming of the axis of ablation and variable spot sizes can correct for any topography of the eye 44 that is abnormal, including non-symmetric topographies. In FIG. 8, one line of a desired treatment topography 190 is illustrated. This could be retrieved, for example, from a computerized eye topography system which indicates various abnormalities in the surface of the eye 44. Using such a topography system, the eye surgery system 10, using the control unit 64, then performs a series of shots, which, for simplicity, are illustrated as eight shots 192 through 206. In actual practice, a far greater number of shots would likely be used. As the system knows the needed ablation at each point, it creates a map of the topography desired and performs ablation using various shot sizes aimed at various points to perform the necessary correction. In this way, a wide variety of non-symmetrical defects of the cornea can be corrected, such as apple and banana shapes, as well as any other abnormal shape.

Figure 9:
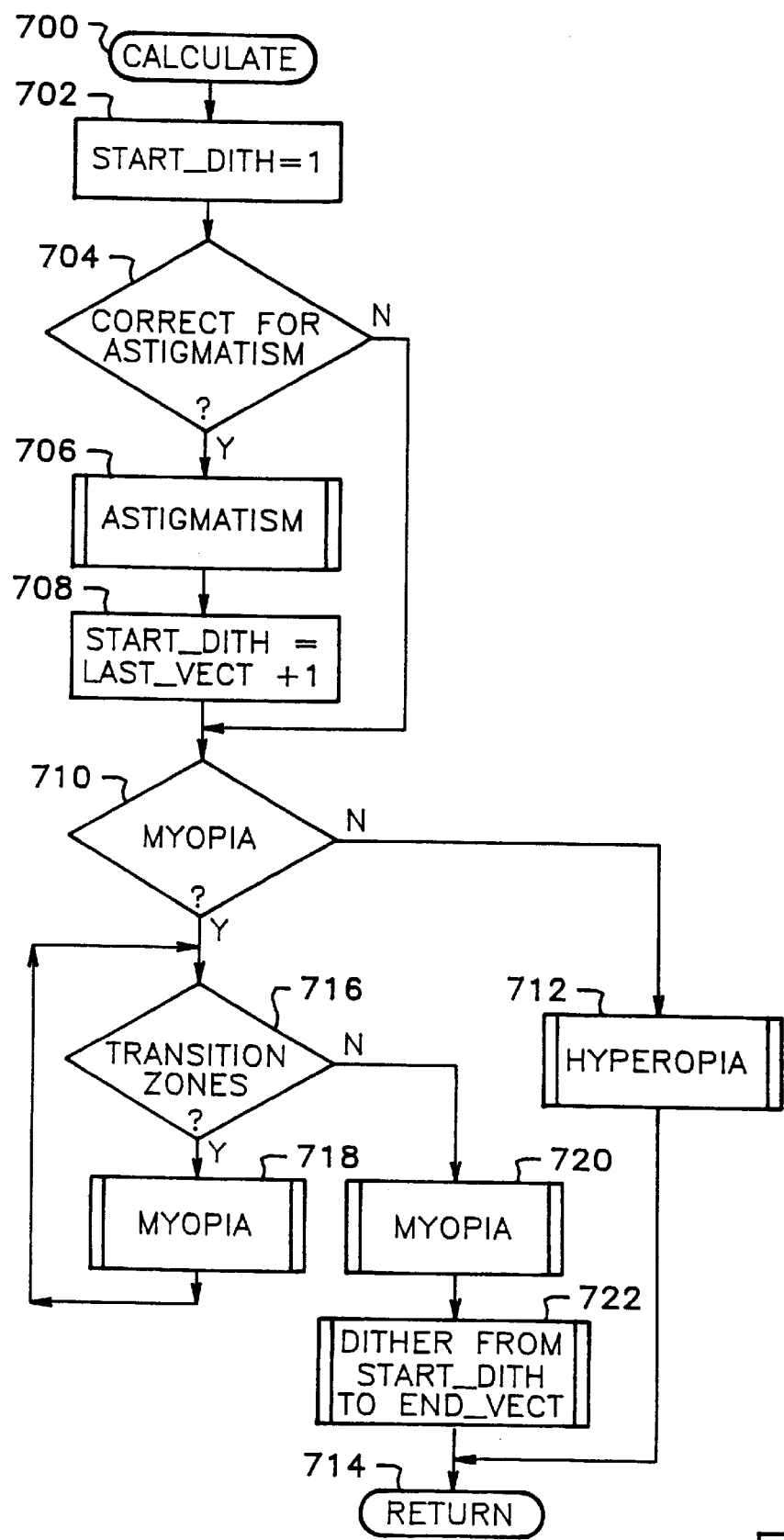
FIG. 9 is a flowchart illustrating a calculation routine used to perform correction for astigmatism, hyperopia, and myopia using the random or circular dithering and large beam scanning according to the invention.

FIG. 9 is a flowchart illustrating a CALCULATE routine 700 that would execute preferably on the control unit 64. The CALCULATE routine 700 calculates a series of shot patterns necessary to perform the desired ablation of the eye 44 to correct for a variety of conditions. In the described embodiment, shot patterns are created to correct for astigmatism, hyperopia, and myopia as described in conjunction with preceding FIGS. 2A to 7. Further, the dithering as illustrated in FIGS. 3 and 4 is applied to myopic correction shot patterns.

Preferably, the CALCULATE routine 700 runs in the control unit 64, which performs the necessary shot calculations before beginning an ablation sequence. By having all the points precalculated, there is no delay in calculation, so each successive shot can be fired in rapid sequence, as soon as the excimer laser 20 is ready. This provides for quicker treatment times and less difficulty in having the patient center on an optical fixation point.

Beginning at step 702, the CALCULATE routine 700 sets a variable START_DITHER to 1. This variable indicates the first ablation shot at which dithering is to begin, and is further discussed below. Note that all of the ablation shots are preferably stored in an array, and START_DITHER indicates a location within that array. Control proceeds from step 702 to step 704, where the routine 700 determines whether astigmatism correction is desired. This is pre-entered by the physician, including both angle of and degree of astigmatic correction, along with the maximum treatment area. As is readily apparent, the routine 700 could also request a degree of curvature for the line of astigmatic correction in the case of non-symmetric astigmatism, and even provide for greater correction towards one or the other ends of the astigmatic region.

If astigmatic correction is desired, control proceeds from step 704 to step 706, where an ASTIGMATISM routine 750 is performed (discussed below in conjunction with FIG. 10), creating the appropriate shot patterns for the desired astigmatic correction. These shot patterns, for example, correspond to those discussed in conjunction with FIGS. 4A and 4B.

Figure 10A:
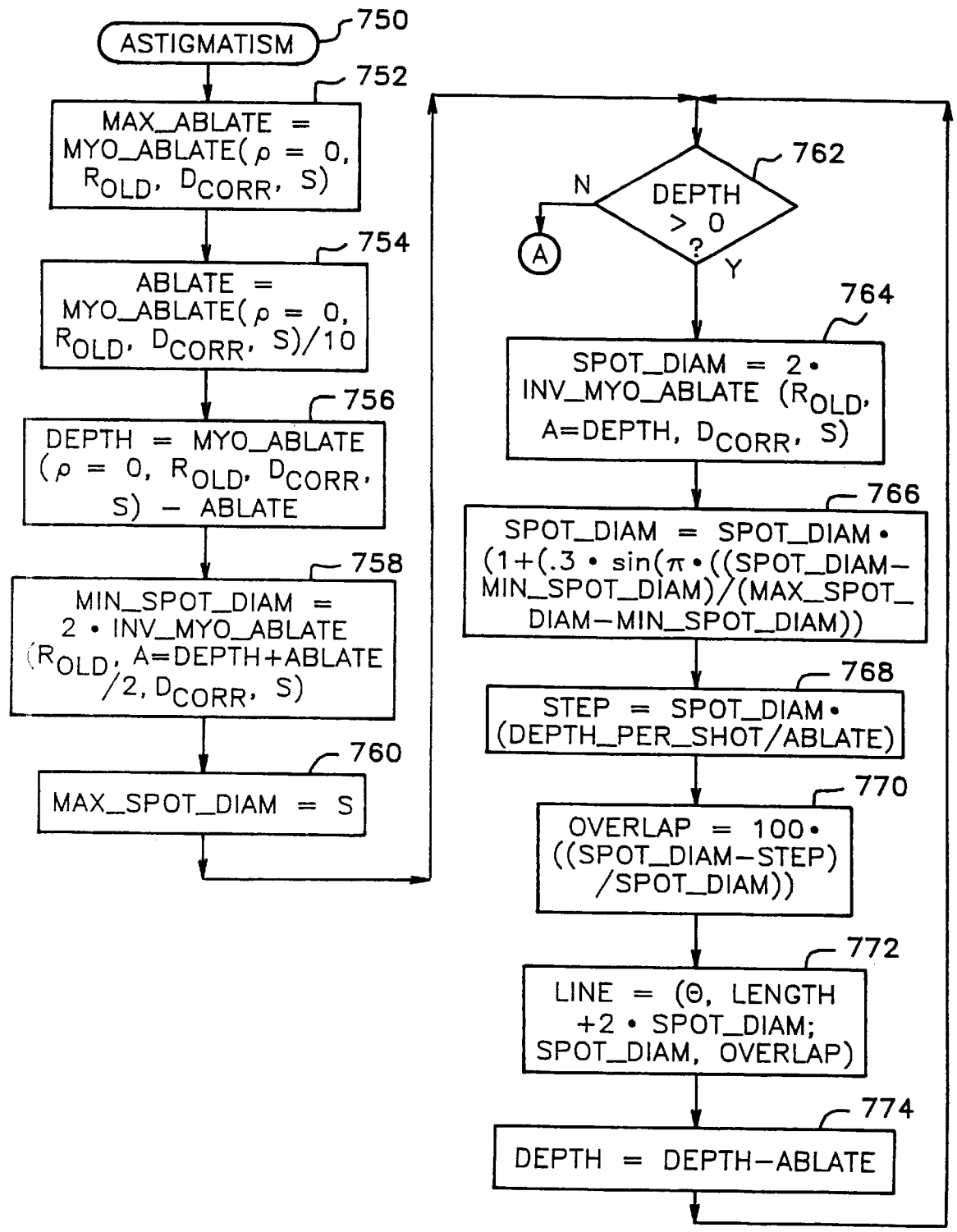
FIGS. 10 and 11 are flowcharts illustrating an astigmatism routine used by the calculation routine of FIG. 9.
Figure 10B:
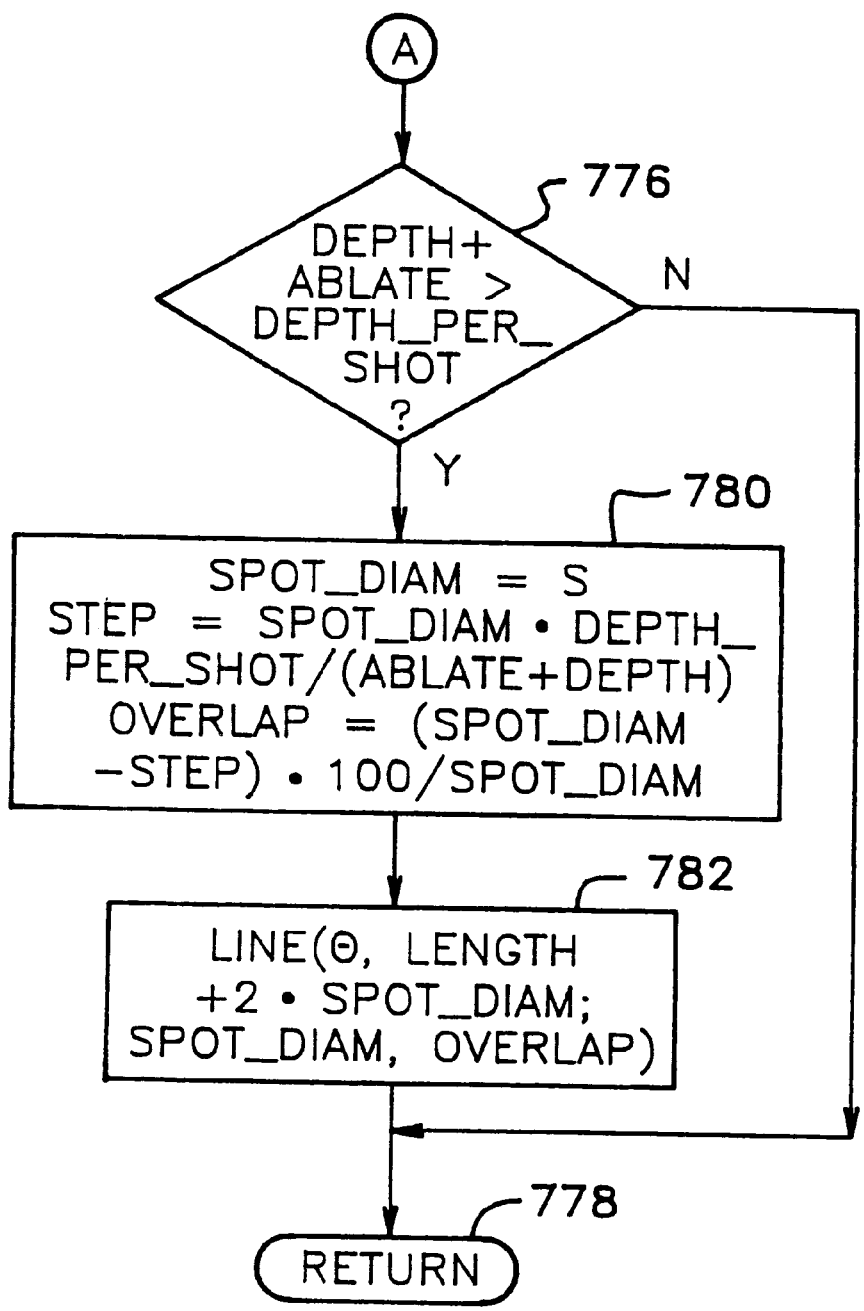

Once the shot pattern for astigmatic correction is calculated at step 706, control proceeds to step 708, where START_DITHER is set to a variable LAST_VECTOR. LAST_VECTOR points to the last calculated shot in the array for an ablation run. In this case, it points to the last vector calculated by the ASTIGMATISM routine 750 (FIG. 10A). Because astigmatism involves overlapping shots rather than potentially reinforcing shots, dithering is preferably not performed during astigmatism correction in the disclosed embodiment, although it could be.

From step 704, if no correction for astigmatism was desired, and from step 708 in any case, control then proceeds to step 710, where the CALCULATE routine 700 determines whether correction for myopia is desired. If not, correction for hyperopia is desired, so control proceeds to step 712 where a HYPEROPIA routine 850 is performed, to be discussed below in conjunction with FIG. 12. As correction for hyperopia is similar to correction for astigmatism, but with the shots in a circle rather than a line, dithering is preferably not performed (although it could be) in the disclosed embodiment, so control then proceeds to step 714, where the routine 700 returns to a master routine, which then allows the physician to begin execution of the shot sequence calculated by the CALCULATE routine 700.

If at step 710 it was determined that correction for myopia is desired, the CALCULATE routine 700 then proceeds to step 716, where it determines whether transition zones are requested. If so, multiple myopic shot series must be formed with the initial "transition zone" series being created by performing a myopia correction. This was discussed above in conjunction with FIG. 2B. So, control proceeds to step 718 where a MYOPIA routine is performed to create a transition zone. This creates a standard myopia correction shot sequence for the transition zone.

Proceeding again to step 716, it is again determined whether more transition zones are required. If the last transition zone shot sequence has been calculated, or if none is needed, control then proceeds to step 720, where the MYOPIA routine is again executed, this time to provide the final correction for myopia.

The creation of series of shot sequences to correct for myopia is well known in the art. Given the necessary depth of ablation as determined by the MYO_ABLATE function described above, a shot pattern is created using appropriate shot sizes to conform to the necessary depth of ablation at each point radiating away from the axis of treatment 102.

Control then proceeds to step 722, where a DITHER routine 940 or 970 is executed as described below in conjunction with FIGS. 13 and 14, performing dithering, or randomizing, on all shots from START_DITHER as set in either step 702 or step 708 to LAST_VECTOR, which was described above in conjunction with step 708. At this point, calculation of the ablation shot sequence is complete, so control proceeds to step 714 where the CALCULATE routine 700 returns to the main program so that the physician can execute the ablation run as is now stored in the array.

FIG. 10 is a flowchart of the ASTIGMATISM routine 750 that is used to calculate the shot vectors necessary to create "trenches" of overlapping lines to correct for a desired dioptric degree of astigmatism along a particular axis. An appropriate number of trenches is created, with each trench preferably using progressively larger spot sizes. Beginning at step 752, the necessary depth of overall ablation is calculated at the deepest part of the series of trenches. This is done using the myopic ablation function MYO_ABLATE, described above in conjunction with FIG. 7A. A variable MAX_ABLATE is set to the value returned by MYO_ABLATE using $\rho=0$, indicating the necessary depth at the center of the trench (the deepest point). Also passed to MYO_ABLATE are the uncorrected radius of curvature $R_{OLD}$, the necessary dioptric correction $D_{CORR}$, and the width of the astigmatism treatment zone S. Note that S is equal to the width of the astigmatism treatment zone, not the length.

Control then proceeds to step 754, where the necessary depth of ablation per trench is calculated. This is preferably calculated as is MAX_ABLATE above, but instead setting a variable ABLATE, which indicates the amount of ablation per trench, to a value equal to MAX_ABLATE divided by 10. This indicates that preferably ten trenches are to be made, although less may be required as the amount of ablation per trench is calculated.

Control then proceeds to step 756, where a variable DEPTH is set equal to the previously calculated MAX_ABLATE minus ABLATE. DEPTH indicates the amount of ablation remaining to be performed to provide the desired degree of correction.

Control then proceeds to step 758, where a minimum spot diameter MIN_SPOT_DIAM is calculated, indicating the smallest spot diameter to be used to create a trench. MIN_SPOT_DIAM is set equal to two times the radius returned by the inverted myopic ablation function INV_MYO_ABLATE. INV_MYO_ABLATE is called with the initial radius of curvature $R_{OLD}$, with A set to DEPTH plus ABLATE/2, with $D_{CORR}$ as the degree of dioptric correction desired, and with S as the width of the treatment zone. The value returned by calling this function is the radius at which 95% of the overall ablation depth needed will be performed, and this radius will preferably be relatively close to the center of the axis of treatment—i.e., the radius will be small compared to the overall width of each trench.

Proceeding to step 760, a maximum spot diameter MAX_SPOT_DIAM is set equal to S, which is simply the width of the astigmatism treatment zone 100 (not the length).

Proceeding to step 762, a loop is entered that creates a series of trenches to provide for the overall degree of correction for astigmatism needed. First, at step 762 it is determined whether DEPTH is greater than zero. Again, DEPTH is the remaining depth necessary to ablate, which will be greater than zero when enough trenches have not been created to provide the desired degree of correction.

If DEPTH is greater than zero, control proceeds to step 764, where the spot diameter SPOT_DIAM is set equal to two times the result returned by INV_MYO_ABLATE, when that function is called with A set equal to DEPTH. This returns the radius at which the ultimate necessary ablation equals DEPTH. As DEPTH is initially nearly equal to the overall depth of ablation needed, the initial spot diameter will thus be small.

Proceeding to step 766, the spot diameter SPOT_DIAM is empirically corrected. This is done by setting SPOT_DIAM equal to $(1+(0.3 \cdot \text{SIN}(\pi \cdot (\text{SPOT\_DIAM}-\text{MIN\_SPOT\_DIAM})/(\text{MAX\_SPOT\_DIAM}-\text{MIN\_SPOT\_DIAM}))))$. This performs an empirical adjustment to the spot diameter to provide better results and better conform the overall correction to the desired curve necessary to correct for astigmatism.

Proceeding to step 768, a variable STEP indicating the amount to move the spot target on each succeeding shot is set equal to SPOT_DIAM·(DEPTH_PER_SHOT/ABLATE). DEPTH_PER_SHOT is the amount of ablation per shot, and is typically 0.2 $\mu$m. Then, at step 770 a variable OVERLAP is set equal to 100·(SPOT_DIAM−STEP)/SPOT_DIAM. This is the amount of overlap in percent needed for each shot.

Proceeding to step 772, a routine LINE 800 is called, discussed below in conjunction with FIG. 11, with $\Theta$ set to the angle at which to create the line of astigmatism, a LENGTH variable set to a predetermined length of the astigmatism series of shots plus 2·SPOT_DIAM, SPOT_DIAM indicating the spot size, and OVERLAP.

The series of shots for the line having been created, control proceeds to 774, where DEPTH is reduced by ABLATE, which is the amount to ablate per trench. Control then loops to step 762, where the reduced value of DEPTH is again compared to zero. This loop is repeated, creating lines of shots with progressively larger spot diameters, until DEPTH is less than zero. DEPTH will be less than zero when virtually all of the ablation shots have been calculated necessary to perform the desired degree of correction.

Once DEPTH is less than zero, control proceeds to step 776 (FIG. 10B), where it is determined whether DEPTH plus ABLATE is greater than DEPTH_PER_SHOT. If not, then another line of ablation should not be performed, as that would provide too much correction, so control then proceeds to step 778 where the ASTIGMATISM routine 750 returns to the CORRECTION routine 700.

If at step 776 the "residue" of ablation still needed does not exceed DEPTH_PER_SHOT, control instead proceeds to step 780. There, SPOT_DIAM is set to the maximum spot diameter of S, which is the width of the treatment zone 100 for the astigmatism line of trenches, STEP is set equal to SPOT_DIAM·DEPTH_PER_SHOT/(ABLATE+DEPTH) and OVERLAP is set equal to (SPOT_DIAM−STEP)·100/SPOT_DIAM.

Control then proceeds to step 782, where a final trench is created using the variables set at step 780 spot width by calling the routine LINE 800. The routine 750 then returns at step 778.

The ASTIGMATISM routine 750 thus creates a shot pattern as described above in conjunction with FIG. 4A.

Figure 11:
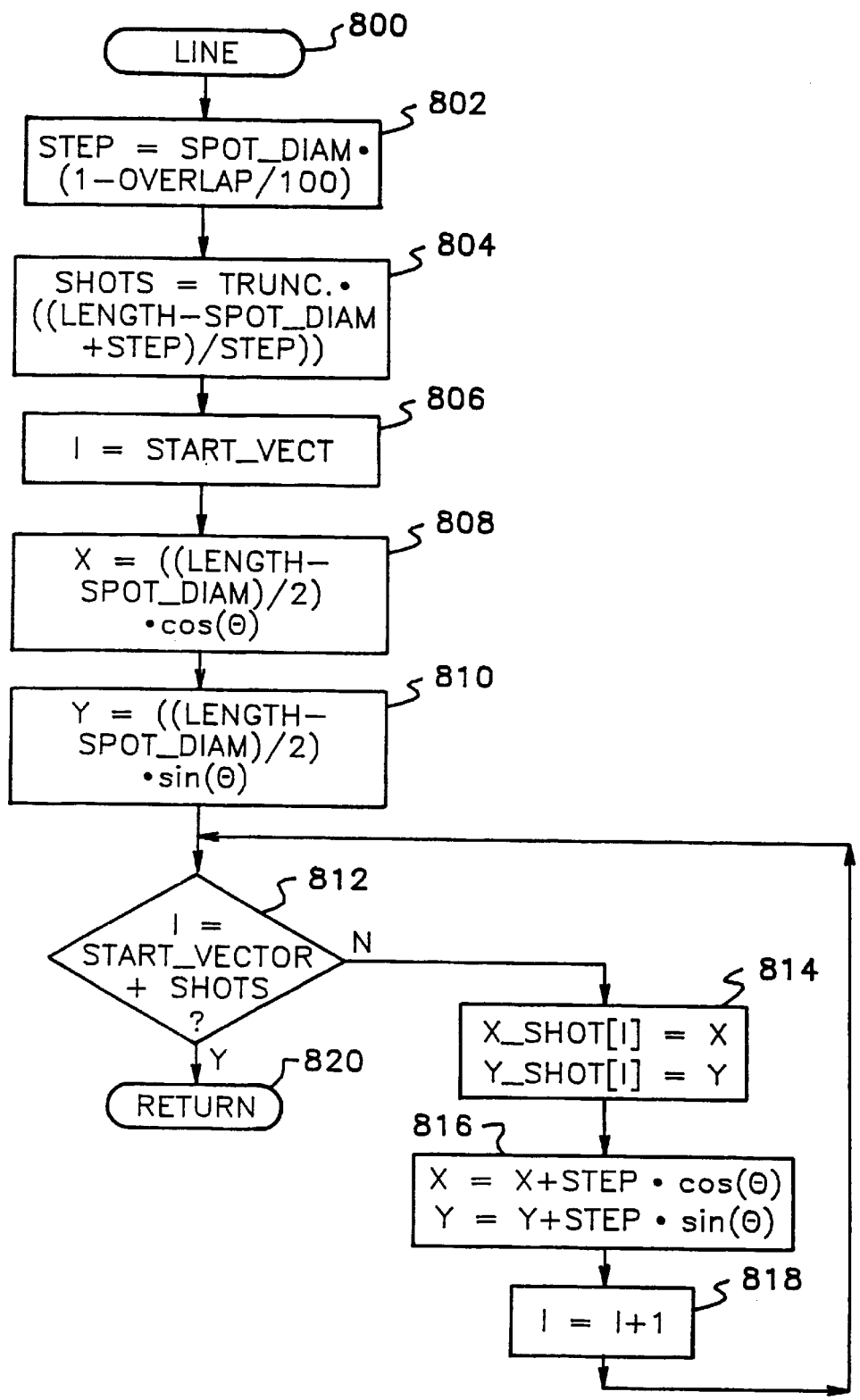

FIG. 11 is a flowchart of the LINE routine 800. This routine 800 calculates the shots for the generation of a line used in creating an astigmatism correction sequence of shots. The desired spot size is passed to the routine 800 in a variable SPOT_DIAM, an overlap percentage is passed in a variable OVERLAP, and the length of the line is determined by a LENGTH variable passed to the LINE routine 800.

Beginning at step 802, the LINE routine 800 first calculates the step size, which is equal to SPOT_DIAM·(1−OVERLAP). Proceeding to step 804, the number of shots required is calculated equal to the truncated value of (LENGTH−SPOT_DIAM+STEP)/STEP. Proceeding to step 806, a counter variable I is set equal to a variable START_VECTOR which is equal to LAST_VECTOR+1. LAST_VECTOR is set equal to I upon completion of the LINE routine 800.

Control then proceeds to step 808, where a variable corresponding to the X axis displacement from the axis of treatment 102 is set equal to ((LENGTH−SPOT_DIAM)/2)·cos θ, where θ is the angle of desired astigmatic correction. In step 810, Y is correspondingly set to ((LENGTH−SPOT_DIAM)/2)·sin θ.

Control then proceeds to step 812, where it is determined whether I equals START_VECTOR plus SHOTS, indicating the end of this line of shots. If not, control proceeds to step 814, where an array location X_SHOT[I] corresponding to the shot location of this particular shot is set equal to X and Y_SHOT[I] is correspondingly set equal to I. Then, at step 816 X is set equal to X+(STEP·cos θ) and Y is set equal to Y+(STEP·sin θ). This is the delta increment required for the next shot.

Control then proceeds to step 818, where I is incremented, and the routine then loops to step 812. Once I is equal to START_VECTOR+SHOTS, indicating the end of this line, the routine returns to the ASTIGMATISM routine 750 at step 820.

Figure 12:
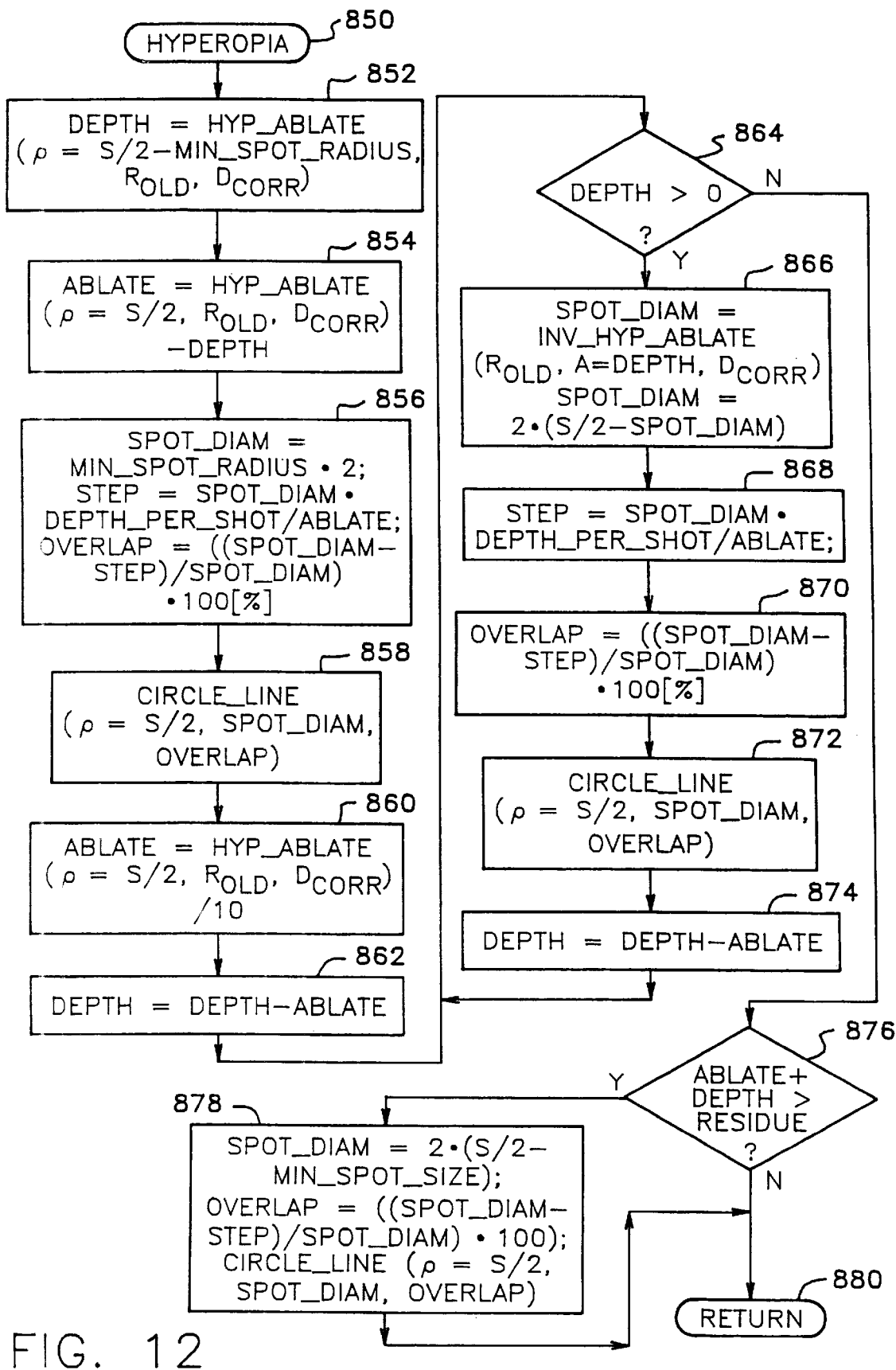
FIG. 12 is a flowchart illustrating a hyperopia routine used by the calculation routine of FIG. 9.

FIG. 12 is a flowchart of the HYPEROPIA routine 850 that creates circular trenches about the axis of treatment 102. It is similar to the ASTIGMATISM routine 750, but creates the circular trenches of an appropriate profile to correct for hyperopia rather than for astigmatism (which uses a myopia correction function).

Beginning at step 852, a variable DEPTH is set equal to the parameter returned by HYP_ABLATE discussed above in conjunction with FIG. 7B, when ρ is set equal to S/2−MIN_SPOT_RADIUS, where S is the diameter of the appropriate area of treatment and MIN_SPOT_RADIUS is the minimum spot size to ever be used for hyperopia ablation, which could be set, for example to 200 μm. HYP_ABLATE is also called with $R_{OLD}$ representing the uncorrected curvature of the eye 44 and D representing the desired degree of dioptric correction. DEPTH thus equals the remaining depth to ablate. It is initially less than the total depth to ablate, as ρ was set just inside the circle of ablation as indicated by S/2 with MIN_SPOT_RADIUS subtracted, which is the first spot radius at which to ablate.

Proceeding to step 854, a variable ABLATE, which indicates the amount to ablate for this hyperopia treatment, is set equal to a parameter returned by HYP_ABLATE called with ρ equal to S/2, with that returned parameter decreased by the amount DEPTH. Thus, ABLATE is the difference in depth at the edge of the area of treatment as indicated by S/2 and the depth at a distance MIN_SPOT_RADIUS just inside that treatment area.

Proceeding to step 856, a variable SPOT_DIAM is set equal to MIN_SPOT_RADIUS·2, a variable STEP is set equal to SPOT_DIAM·DEPTH_PER_SHOT/ABLATE, and a variable OVERLAP is set equal to ((SPOT_DIAM−STEP)/SPOT_DIAM)·100 (i.e., expressed as percent). Thus, the first circular trench will be shot using the minimum spot diameter as indicated by MIN_SPOT_RADIUS·2.

Proceeding to step 858, a routine CIRCLE_LINE is called which calculates the series of shots necessary to ablate a circular trench given the variables SPOT_DIAM, STEP, and OVERLAP. The CIRCLE_LINE routine directly corresponds to the LINE routine 800, except that the circle is shot at a fixed radius given by S/2, instead of being shot along a line. Its implementation corresponds to the LINE routine 800, with the exception that each succeeding shot is incremented along the radius of ρ equal to S/2, rather than along a line.

Proceeding to step 860, ABLATE is set equal to a parameter returned by HYP_ABLATE when HYP_ABLATE is called with ρ equal to S/2, with that returned parameter then divided by 10. This corresponds to preferably ten trenches being ablated to form the appropriate profile of curvature to correct for hyperopia.

Proceeding to step 862, DEPTH is then set to DEPTH minus ABLATE, which reduces DEPTH by 1/10th of the total depth needed to ablate the hyperopic trench.

The routine 850 then proceeds to step 864, where it is determined whether DEPTH, which indicates the total depth remaining to ablate, is greater than zero. If so, then there remaining trenches to ablate, so the routine proceeds to step 866, where SPOT_DIAM is set equal to the parameter returned by INV_HYP_ABLATE when that function is called with A equal to DEPTH. This then returns the radius at which ablation must occur to a depth equal to the current value of DEPTH in order to provide the appropriate correction for hyperopia. This returned parameter, however, is a radius from the axis of treatment 102. To calculate the actual spot diameter, SPOT_DIAM is set equal to 2·(S/2−SPOT_DIAM). This sets SPOT_DIAM to two times the difference of the radius of the actual zone of treatment minus the radius at which the current ablation depth is to occur. This difference in radii times two is thus equal to the spot diameter for the current trench to ablate.

Proceeding to step 868, STEP is set equal to SPOT_DIAM·DEPTH_PER_SHOT/ABLATE. Proceeding to step 870, OVERLAP is set equal to ((SPOT_DIAM−STEP)/SPOT_DIAM)·100, which sets the appropriate overlap in percent.

Using these values of SPOT_DIAM and OVERLAP, and with ρ equal to S/2, at step 872 the routine CIRCLE LINE is called, creating a circular trench. Proceeding to step 874, DEPTH is again set equal to DEPTH minus ABLATE. The routine then loops to step 864, and continually loops through steps 866 through 874 until DEPTH is not greater than zero.

When DEPTH is not greater than zero at step 864, the routine 850 proceeds to step 876, where it is determined whether ABLATE plus DEPTH is greater than RESIDUE, where RESIDUE is an arbitrary value at which another trench is not to be ablated. This value is preferably 500 microns, although could be a different value. If ABLATE plus DEPTH is greater than RESIDUE, then more than that RESIDUE value remains to be ablated, so the routine 850 proceeds to step 878, where a final trench is created using a SPOT_DIAM of 2·(S/2−MIN_SPOT_SIZE) and an OVERLAP of ((SPOT_DIAM−STEP)/SPOT_DIAM)·100. Then from step 876 and step 878, the routine returns at step 880.

Figure 13:
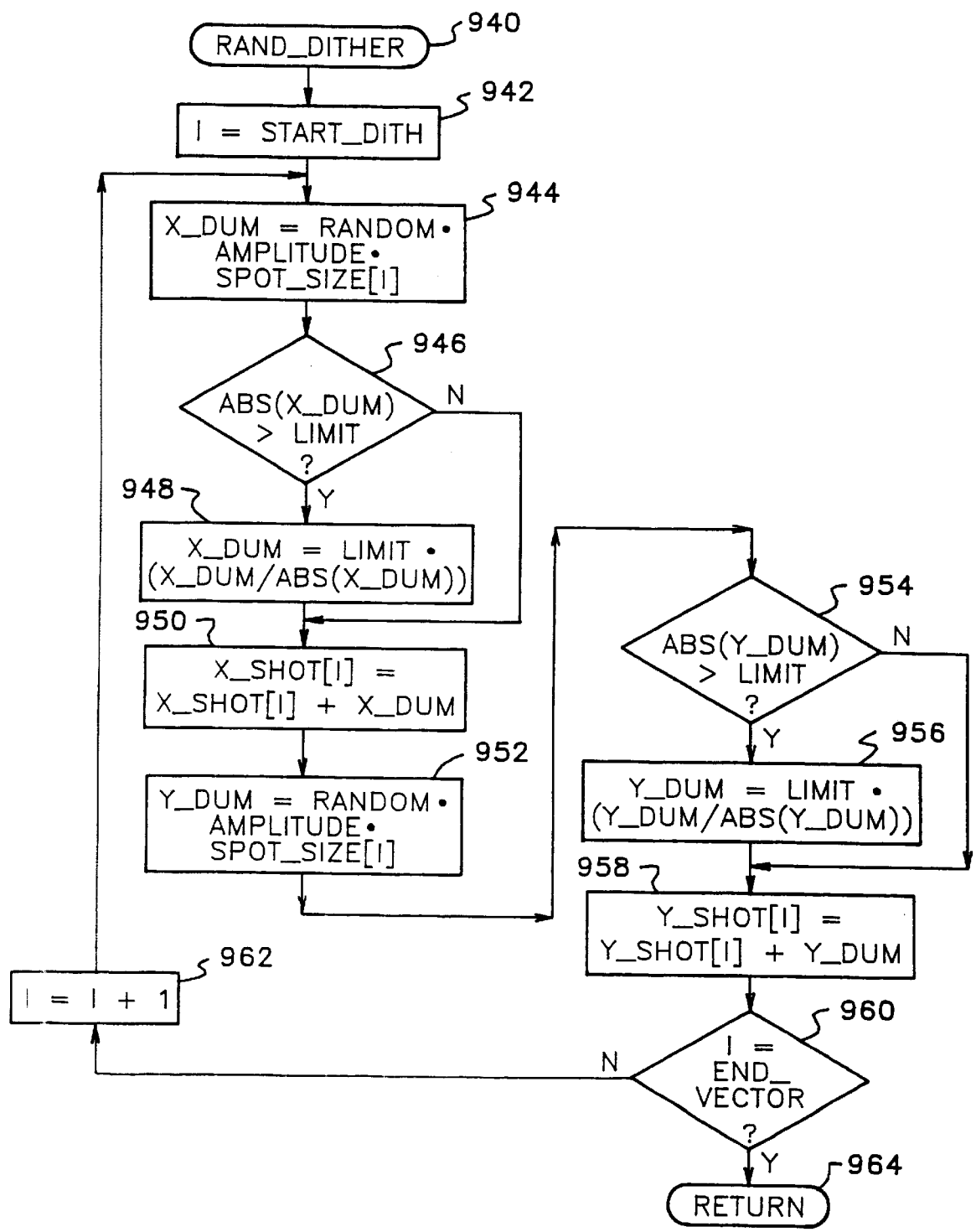
FIG. 13 is a flowchart of a random dithering routine used by the calculation routine of FIG. 9.
Figure 14:
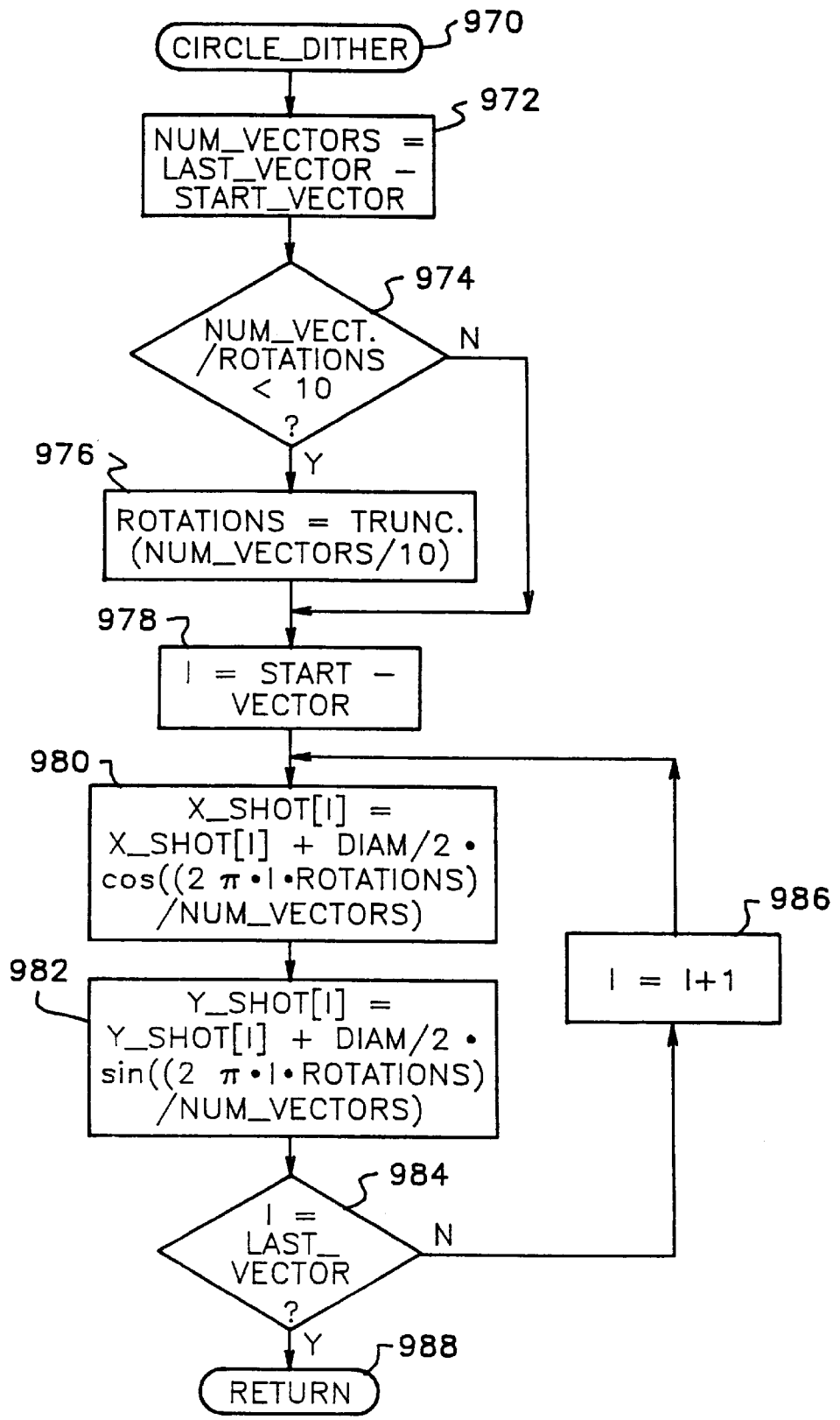
FIG. 14 is a flowchart of a circular dithering routine used by the calculation routine of FIG. 9.

FIG. 13 is a flowchart of a RAND_DITHER routine 940 which corresponds to the DITHER routine as noted in step 722 of FIG. 9. The RAND_DITHER routine 940 randomly dithers all vectors in the described array from START_DITH to LAST_VECTOR. START_DITH was previously set at step 702 or step 708 of FIG. 9 to be equal to the first array location following shots used for correction of astigmatism. Thus, dithering is preferably applied to the myopia correction, rather than to the astigmatism correction. The RAND_DITH routine 970 creates a shot pattern as is illustrated in FIG. 3A.

The RAND_DITHER routine 940 begins at step 942 by setting a counter variable I to START_DITH. Control then proceeds to step 944, where an intermediate variable X_DUM is set equal to a random number RANDOM between −0.5 and 0.5 times AMPLITUDE times SPOT_SIZE[I]. The variable AMPLITUDE was passed to the RAND_DITHER routine 940 as indicating the appropriate amplitude of dithering in fractional percentage of spot size, and SPOT_SIZE[I] corresponds to the spot size for this particular shot.

Control then proceeds to step 946, where the routine 940 determines whether the absolute value of X_DUM is greater than a limiting size denoted by a variable LIMIT, which is predetermined by the system. If X_DUM is too large, control then proceeds to step 948, where X_DUM is set equal to LIMIT X_DUM/ABS(X_DUM), which sets X_DUM to LIMIT with the appropriate sign appended.

If X_DUM was not too large in step 946, and in any case from step 948, control then proceeds to step 950, where X_SHOT[I] is set equal to X_SHOT[I]+X_DUM, which provides a random dithering effect according to the invention. Control then proceeds to steps 952, 954, 956, and 958, where Y_SHOT[I] is adjusted with the random dithering as X_SHOT[I] was dithered at steps 944 through 950.

Control then proceeds from step 958 to step 960, where the RAND_DITHER routine 940 determines if I=LAST_VECTOR, indicating that the last vector desired has been dithered. If not, control proceeds to step 962, where I is incremented, and control then loops to step 944 to process the next shot.

If at step 960 I equals LAST_VECTOR, the RAND_DITHER routine 940 is complete, so the routine 940 then returns at step 964.

Figure 19:
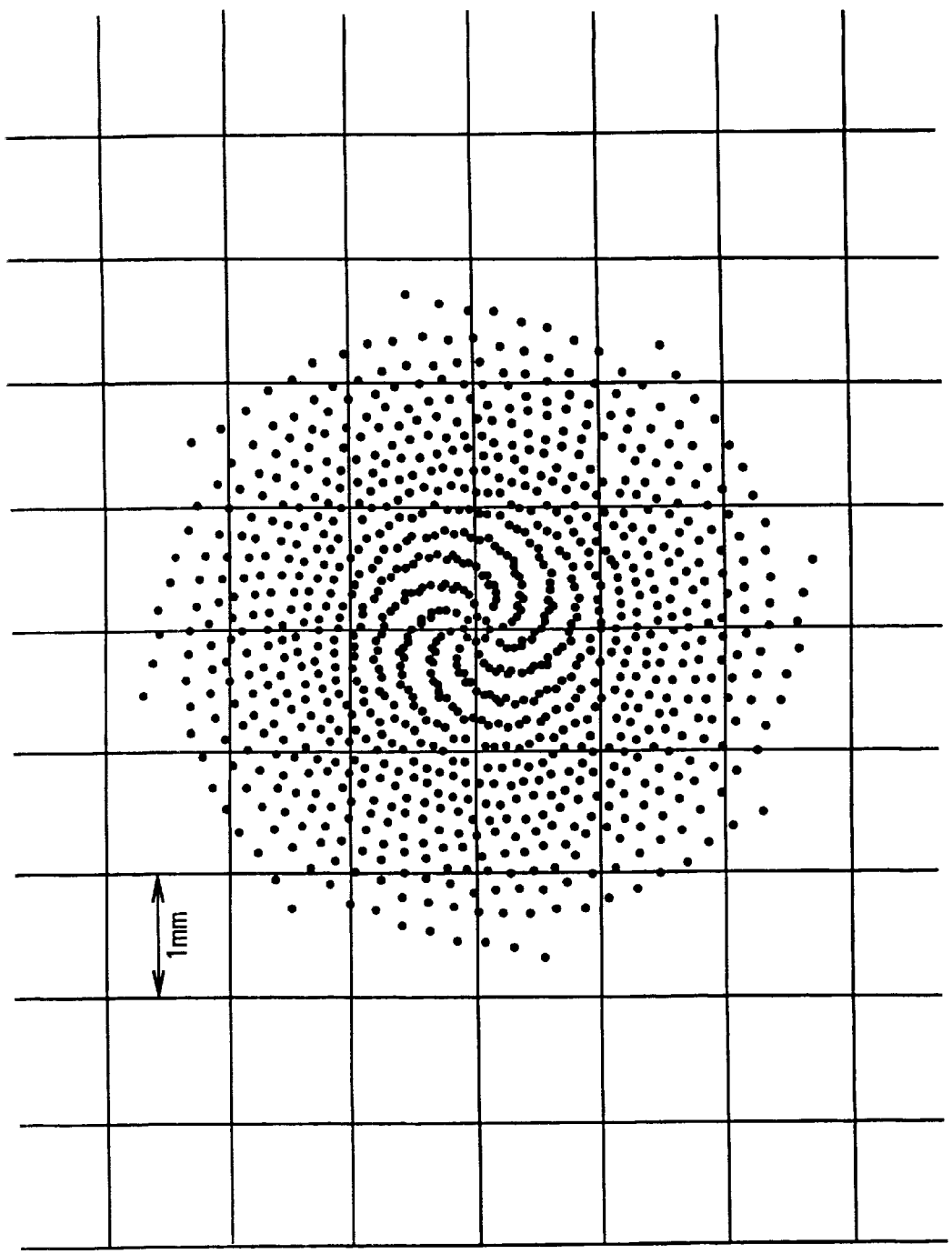
Figure 20:
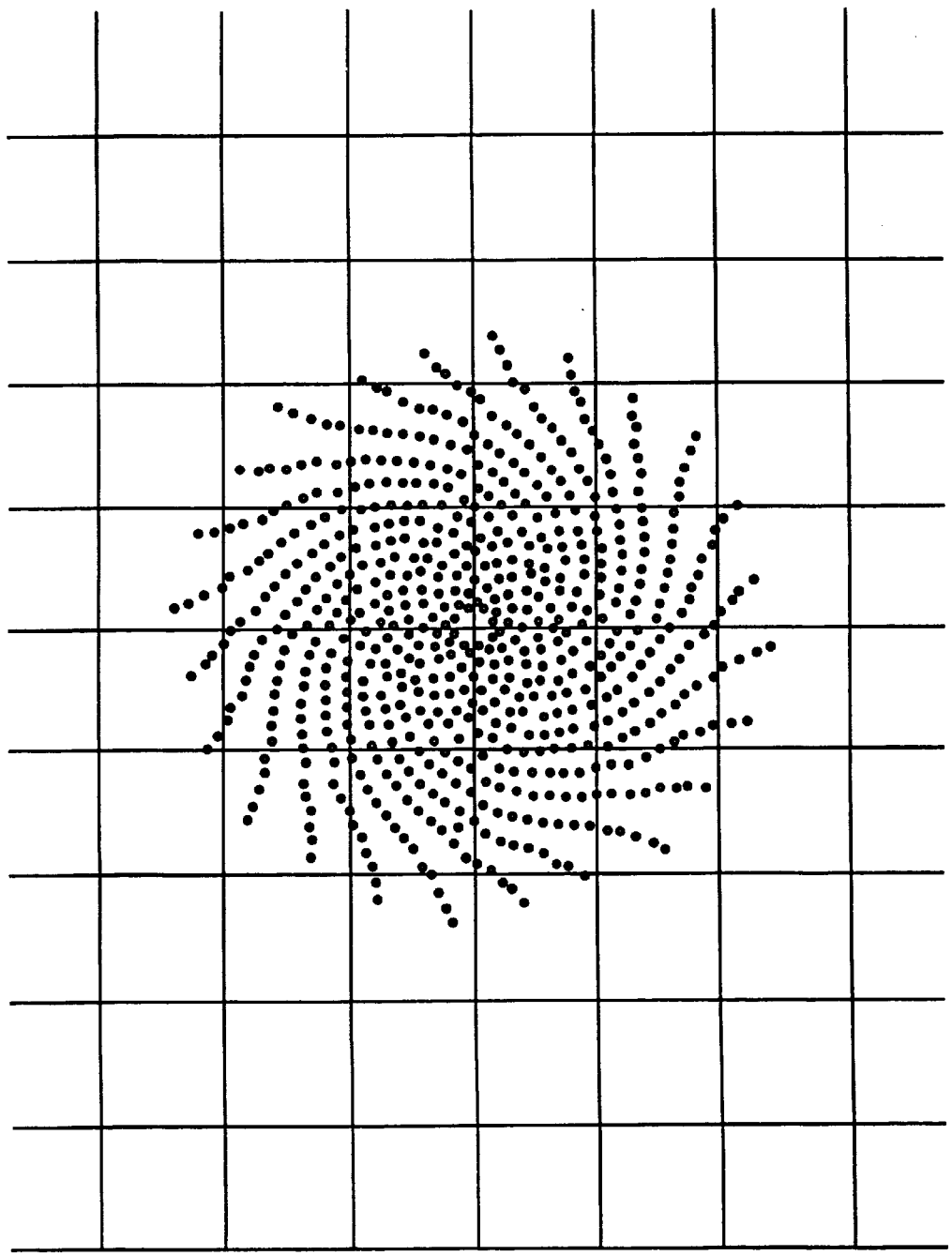
Figure 21:
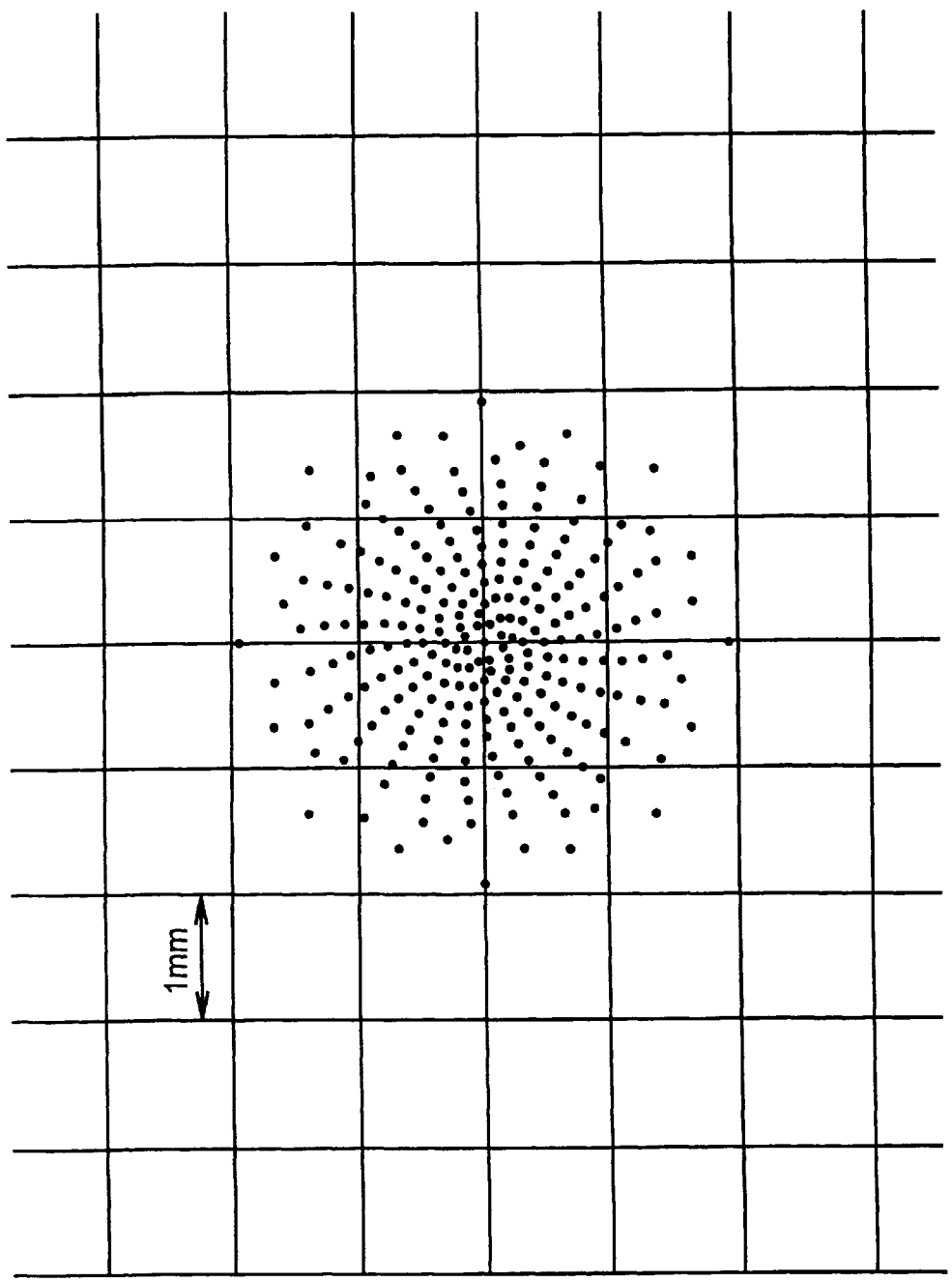
Figure 22:
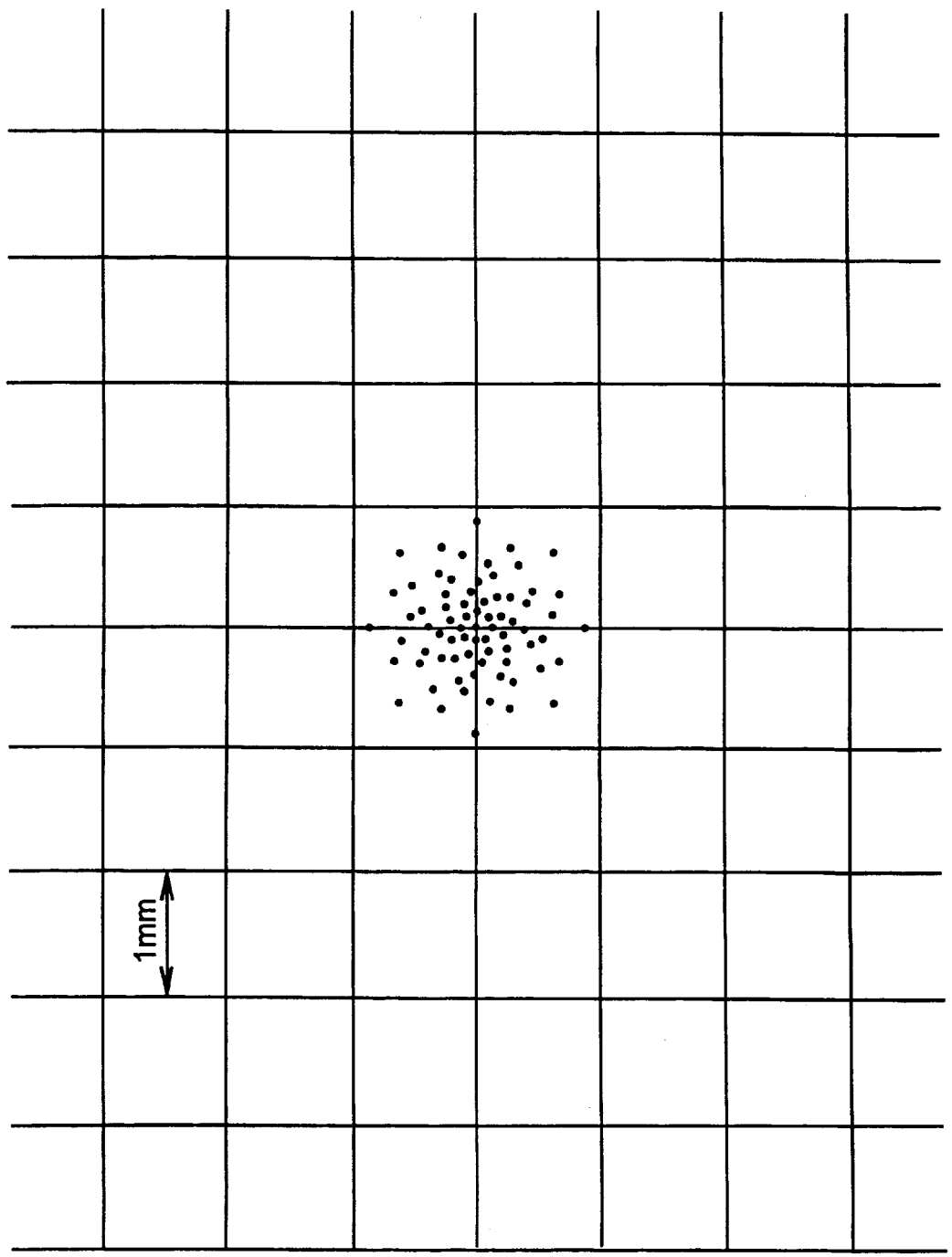
Figure 23:
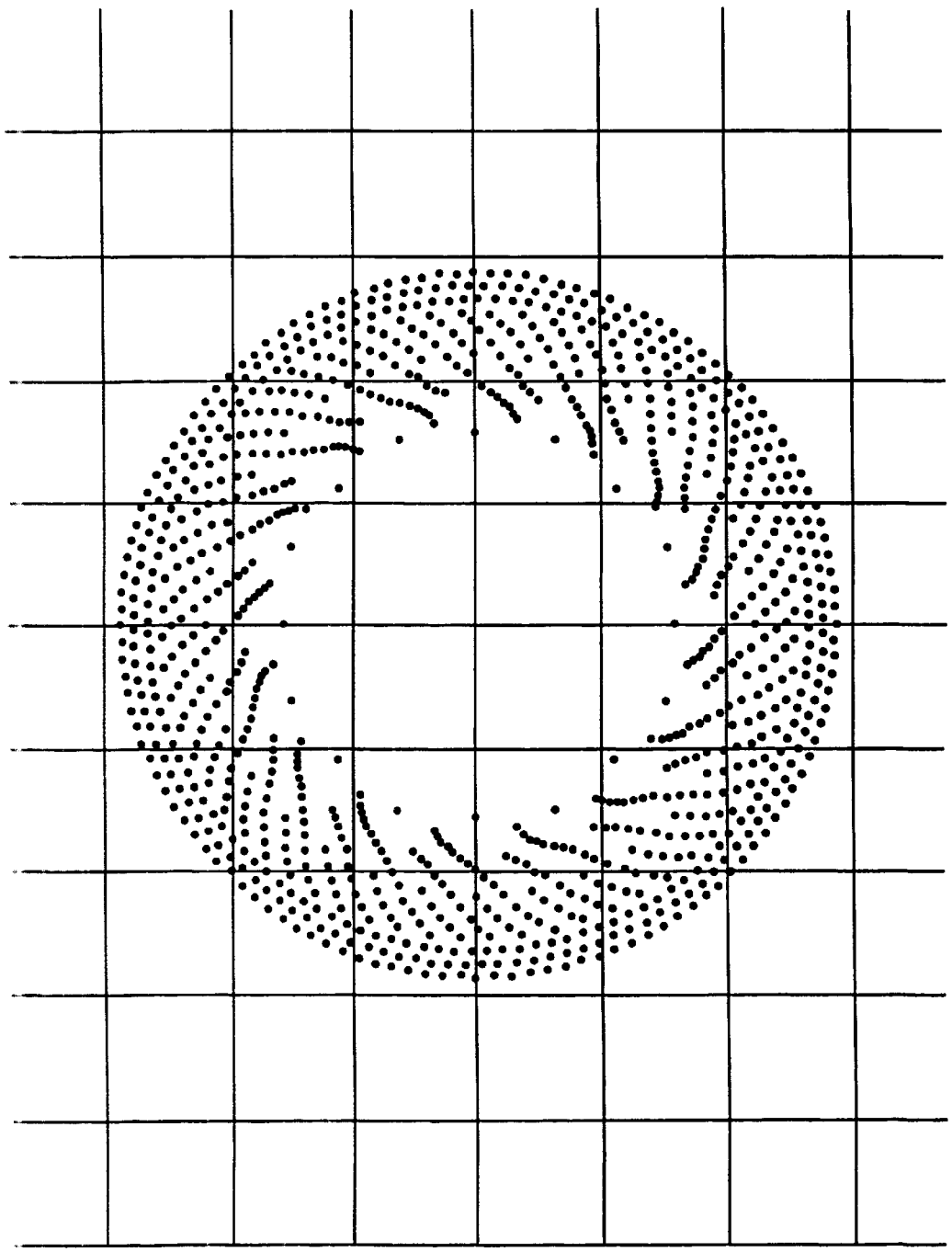
Figure 25:
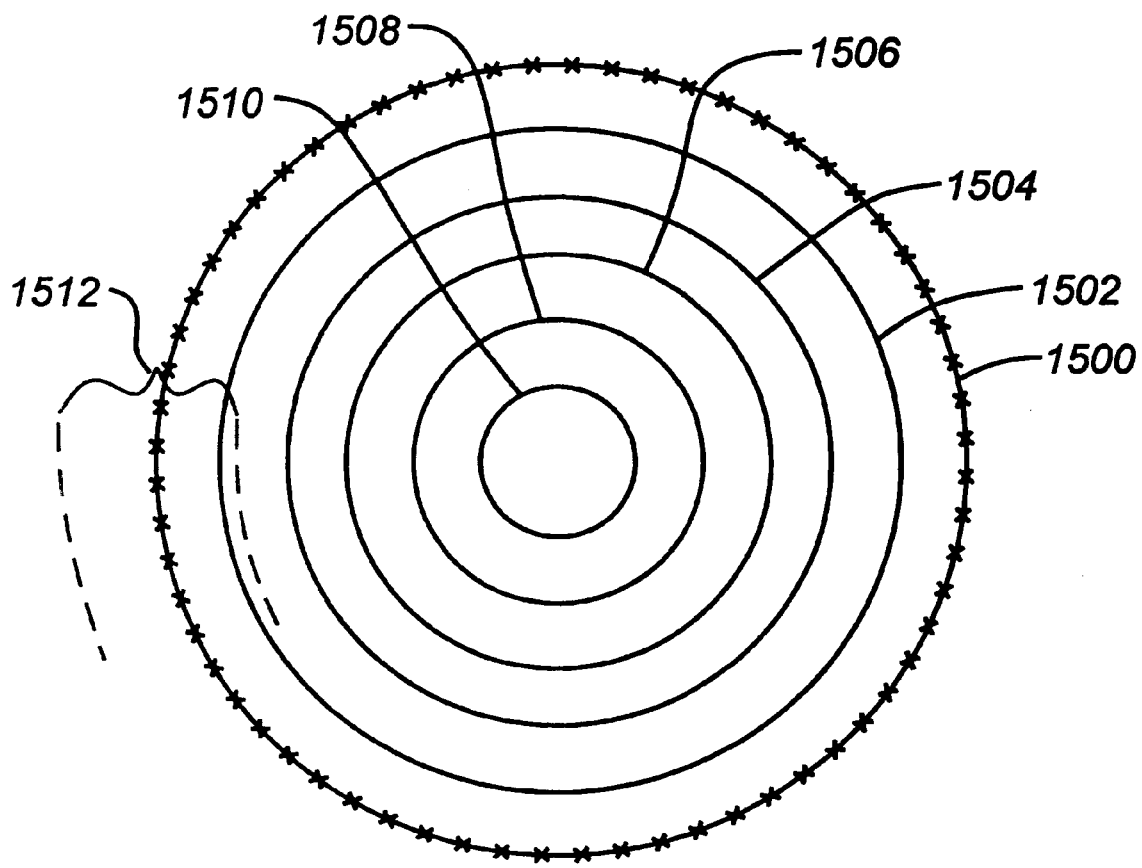
Figure 26:
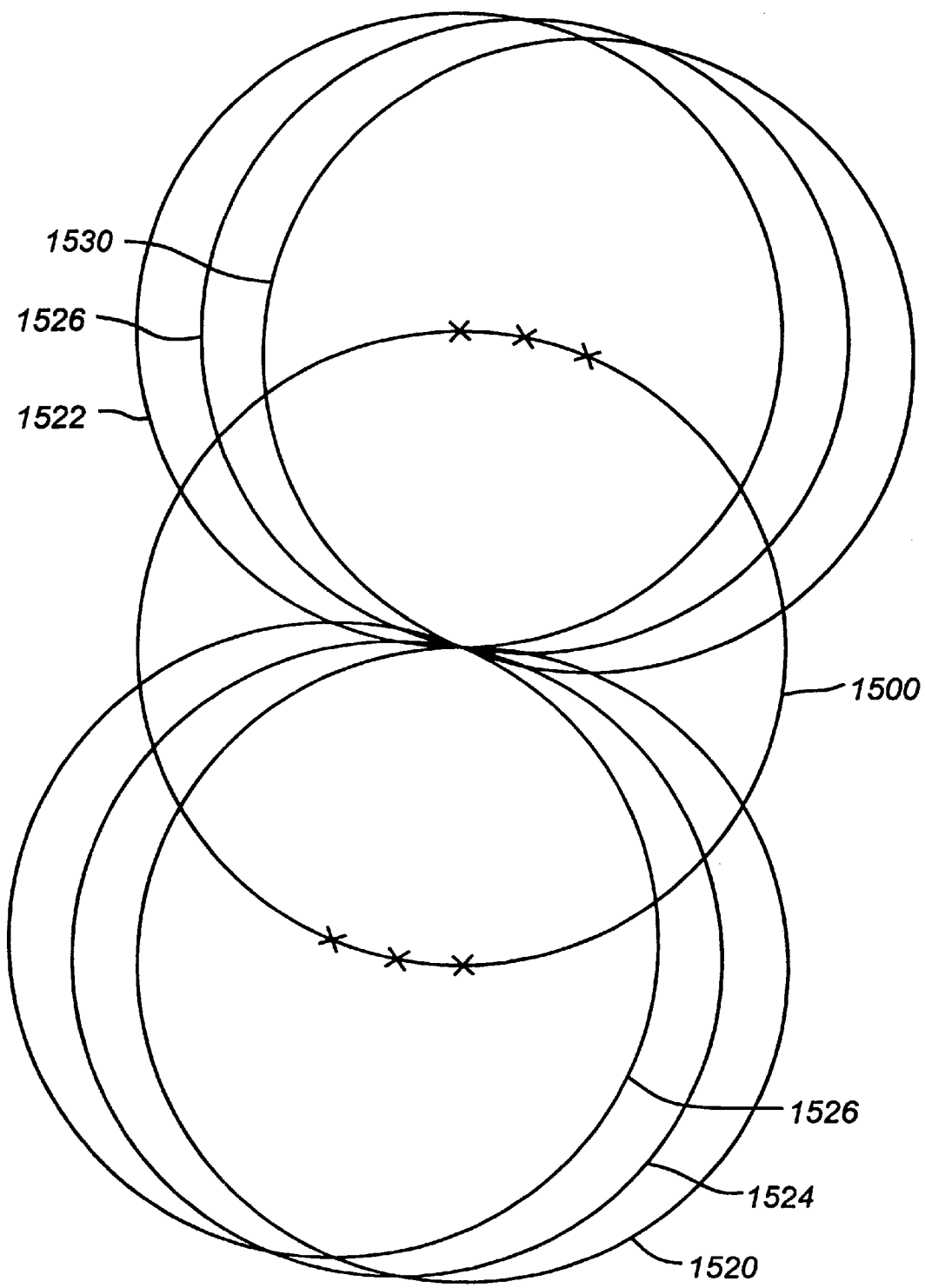
Figure 27:
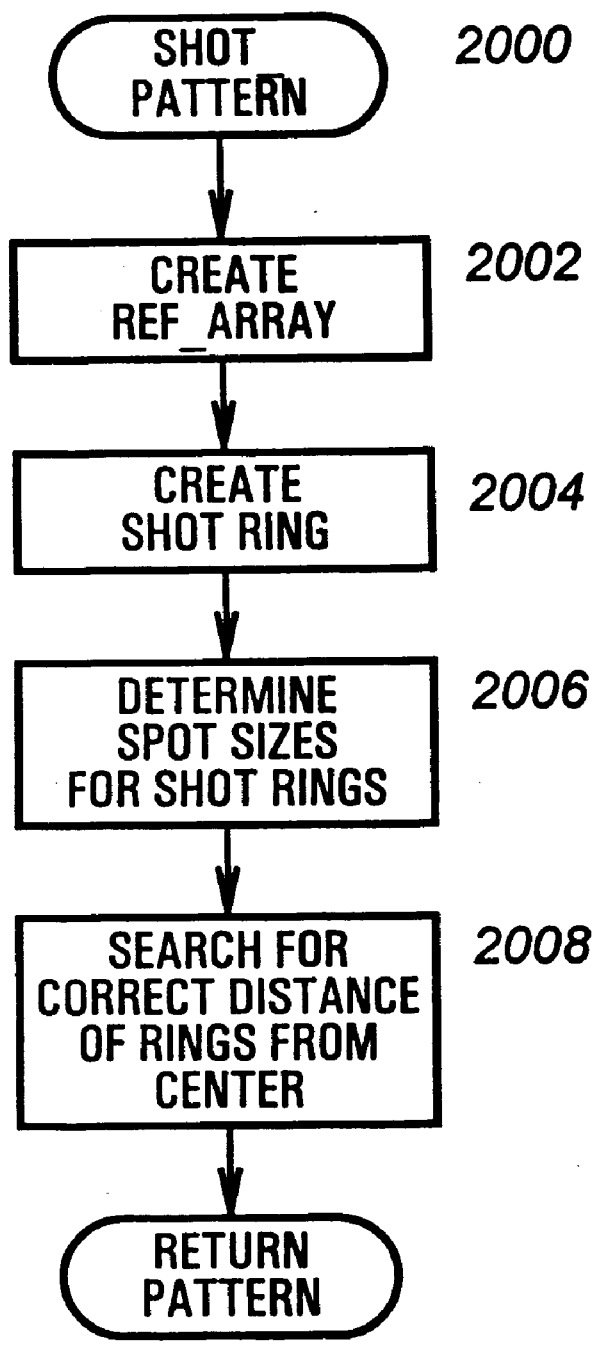
Figure 28:
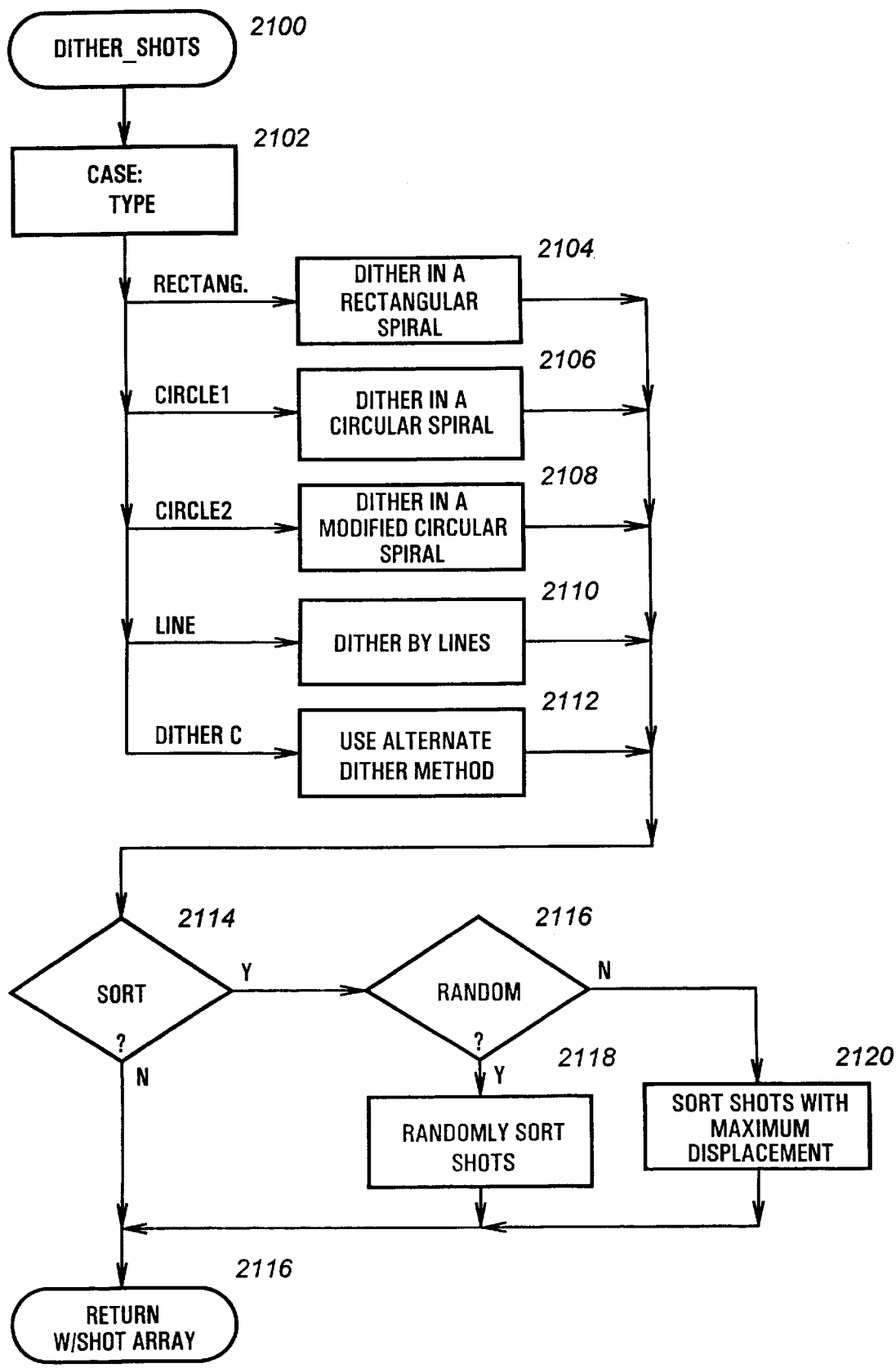

FIG. 19 shows an alternative routine CIRCLE_DITH 970, which can be used instead of the RAND_DITH routine 940. A shot pattern as created by the CIRCLE_DITH routine 970 is illustrated in FIG. 3B. The CIRCLE_DITH routine 970 begins at step 972, where a variable NUM_VECT is set LAST_VECTOR−START_VECTOR, both of which were passed by the calling routine. Proceeding to step 974, it is determined whether NUM_VECT/ROTATIONS is less than 10. The variable ROTATIONS is passed to the routine 970 to indicate how many circular rotations to make around the axis of treatment 102 in adjusting all of the shots. The check is made at 974 to prevent an excessive number of rotations if there are insufficient shots. For example, if there are only twenty vectors, ten revolutions would result in two sets of ten shots each 180° apart. By arbitrarily requiring NUM_VECT/ROTATIONS to be at least 10, this prevents such accumulation of shots, requiring the shots be distributed over at least ten different points around the axis of treatment 102. If NUM_VECT/ROTATIONS is less than 10, control proceeds to step 976, where ROTATIONS is set equal to the truncated value of NUM_VECT/10. From step 976 and 974, if that step was not true, control then proceeds to step 978, where I is set equal to START_VECTOR.

Control then proceeds to step 980, where X_SHOT[I] is set equal to X_SHOT[I]+(DIAM/2)·cos((2π·I·ROTATIONS)/NUM_VECT). This circularly adjusts the center of each shot. Y_SHOT[I] is correspondingly adjusted in step 982.

From step 982, control proceeds to step 984, where it is determined whether I is equal to LAST_VECTOR. If not, control then proceeds to step 986 where I is incremented for another pass through steps 980 and 982 to adjust subsequent vectors.

If from step 984 I is equal to LAST_VECTOR, control then proceeds to step 988, where control returns to the CALCULATE routine 700.

It will be readily appreciated that this dithering, or oscillation, could also be applied one dimensionally, and could be used for hyperopia and astigmatism correction as well.

Figure 15:
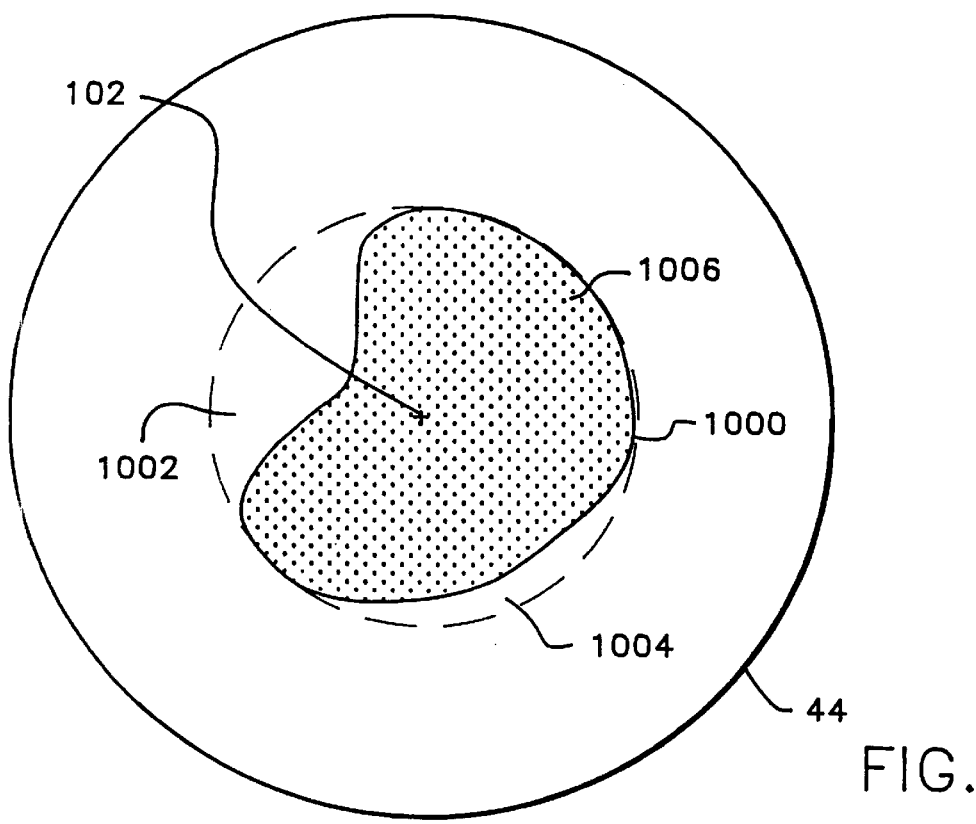
FIGS. 15 and 16 are views along the axis of treatment of the eye illustrating ablation of the epithelium according to the invention.

FIG. 15 illustrates an image returned by the video unit 56 in performing epithelia ablation using infrared dye and using the scanning large beam according to the invention. The epithelium is typically approximately 50 $\mu$m thick. As the preferred excimer laser 20 used in the system S according to the invention ablates approximately 0.2 $\mu$m per shot, 250 initial shots will typically be needed until the epithelium has been ablated. At some time before that point, however, variations of the epithelia thickness come into play. For example, some points might be 40 $\mu$m thick, while others are 60 $\mu$m thick.

The system S according to the invention removes the epithelium by sensing when it has completely removed at least a portion of the epithelium, and then selectively removing the remainder. FIG. 15 illustrates an epithelial removal zone 1000 in which a predetermined number of shots have been previously performed using a spot size the size of the epithelial removal region 1000. After each shot, the infrared video unit 56 captures any infrared fluorescence emitted from the eye 44. This fluorescence is created by first dyeing the epithelium with an infrared fluorescent dye that does not dye the layers underlying the epithelium. This dye is preferably infrared fluorescent to reduce the possibility of a pumped lasing action into the eye 44 of damaging frequencies of light at damaging energies. Other dyes could be used, including visible light emitting dyes, if it is ensured that no pumped lasing action will occur that might damage the eye 44. Infrared fluorescent dye is also preferred to prevent any distracting optical affects to the patient while the epithelium is being ablated.

After a predetermined number of shots, the video unit 56 will detect some portion of the epithelial removal region 1000 that does not fluoresce. This indicates that there is no infrared fluorescent dye at that location, which correspondingly indicates the epithelium has been entirely ablated at that point.

In FIG. 15, two regions 1002 and 1004 are shown in which all of the epithelium has been removed by the predetermined number of shots. At this point, the spot size is reduced, and a region 1006 in which the epithelium still remains, as indicated by the infrared fluorescent dye, is further ablated.

Figure 16:
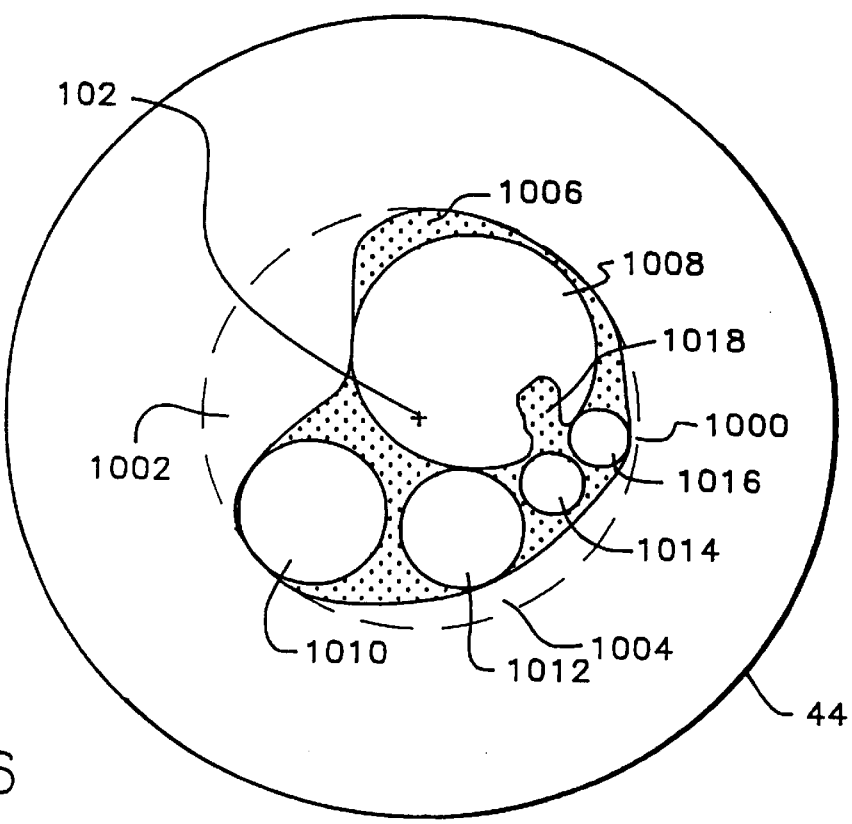

Either under computer control or under physician control, the selective ablation is performed as illustrated in FIG. 16. In FIG. 16, the remaining region 1006 has been further ablated using reduced spot sizes, forming further epithelial free regions 1008, 1010, 1012, 1014, and 1016. The video unit 56 further observes the epithelial removal region 1000 during ablation of each of these remaining regions, detecting when a certain portion of those regions do not fluoresce. Again, differences in epithelial depth across each of these regions can result in only partial ablation of the epithelium in these remaining regions. For example, an island 1018 of epithelium is shown remaining in the region 1008 which has been further ablated. Such islands must be further ablated, along with any remaining portion of the epithelium 1006 which has not been removed by the subsequent ablation.

It will be recognized that by keeping a computer map of the epithelial removal region 1000, along with the number of shots fired onto each particular point in that region, a map of epithelial thickness can be created. By knowing the ablation depth of each shot, along with where each shot has been fired, it is known how many shots a particular point receives before all of the epithelium is removed from that region. Thus, a map of the thickness of the epithelium is created. This map would be similar to that created in correcting for non-symmetrical optical aberrations as discussed in conjunction with FIG. 8.

It will be appreciated that the large beam scanning and dithering according to the invention need not only be applied to the surface of the eye 44. For example, U.S. Pat. No. 4,903,695, entitled "Method and Apparatus for Performing a Keratomileusis or the Like Operation," issued Feb. 27, 1990, discloses a method of removing a portion of the cornea from the eye and then ablating the exposed surface. Thus, the method and apparatus according to the invention can also be used on the exposed surface resulting from such a keratomileusis type procedure. In such a case, the axis of treatment 102 would fall either on either the severed portion of the cornea or on the surface of the cornea from which a portion had been severed.

The foregoing disclosure and description of the invention are illustrative and explanatory thereof, and various changes in the size, shape, materials, components, circuit elements, and optical components, as well as in the details of the illustrated system and construction and method of operation may be made without departing from the spirit of the invention.

What is claimed is:

1. An eye surgery system for shaping the cornea of the eye, comprising:
   a laser that emits a light beam having a propagation axis;
   an optical system cooperating with the laser that directs the light beam to the cornea forming a light spot on a surface of the cornea, wherein the propagation axis of the light beam at the cornea locates the position of the light spot on the corneal surface; and
   a control unit in cooperation with the optical system that controls a light spot sizing component of the optical system to create a selectively variable size of the light spot on the corneal surface and a propagation axis directing component of the optical system for locating the beam spot at a selective plurality of locations on the corneal surface, wherein the control unit regulates the size of the light spot in correlation to the selective directing of the beam propagation axis.

2. The eye surgery system of claim 1, wherein a maximum size of the light spot on the cornea is limited by the control unit to a light spot area between approximately 10% and approximately 90% of a total treatment area of a region of the cornea from which tissue is to be removed to achieve a desired vision correction profile.

3. The eye surgery system of claim 2, wherein the maximum size of the light spot area is between approximately 20% and approximately 80% of the total treatment area.

4. The eye surgery system of claim 1, wherein the maximum size of the light spot is limited by the control unit in a manner that depends on the shape and the size of the region from which tissue is to be removed.

5. The eye surgery system of claim 1, wherein the optical system comprises a scanning mirror that scans the spot over the cornea.

6. The eye surgery system of claim 5, wherein the control unit is adapted to move the scanning mirror such that the light spot on the cornea oscillates from shot to shot in at least one direction.

7. The eye surgery system of claim 5, wherein the scanning mirror has a motion that moves a propagatin axis of the light spot over a conic-shaped shell surface.

8. The eye surgery system of claim 7, wherein the mirror motion produces a circular pattern of overlapping shots projected onto the eye.

9. The eye surgery system of claim 7, wherein the optical system comprises a diaphragm located in an optical path of the beam that forms the light spot, further wherein the diaphragm produces a homogeneous energy distribution over the light spot area deposited on the eye during movement of the axis of the light on the conic-shaped shell surface.

10. The eye surgery system of claim 9, wherein the diaphragm is rotatably mounted to rotate asynchronously with respect to the movement of the axis of the light on the conic-shaped shell.

11. The eye surgery system of claim 5, wherein the optical system comprises a diaphragm that forms the shape of the light spot, located in a optical path of the beam in a location before or after the scanning mirror.

12. The eye surgery system of claim 11, wherein the diaphragm has a controlled motion synchronous with the movement of the scanning mirror.

13. The eye surgery system of claim 11, wherein the diaphragm has a shape that produces a non-axially symmetric laser spot shape.

14. The eye surgery system of claim 5, wherein the scanning mirror can tilt about at least one axis.

15. The eye surgery system of claim 1, wherein the laser is an excimer laser having a pulsed output beam.

16. The eye surgery system of claim 1, wherein the optical system comprises an adjustable diaphragm located in an optical path of the beam to allow for adjustment of a shape and an area of the beam spot, and further comprising a spot mode lens retractably positioned in the beam path to effect one of a desired therapeutic treatment and a desired refractive treatment.

17. The eye surgery system of claim 1, wherein the selectively controlled light spot position generates a controlled axisymmetric ablation profile.

18. The system of claim 1, further comprising a second laser having a visible light beam propagation pathway at least partly coincident with the propagation axis of the light beam.

19. The system of claim 18, wherein the second laser light beam propagation pathway is centered on an axis of treatment of the eye.

20. The system of claim 18, wherein the second laser emits a continuous wave laser beam.

21. The system of claim 20, wherein the second laser beam has a wavelength that does not ablate corneal tissue.

22. The system of claim 21, wherein the second laser beam wavelength is in the red part of the visible spectrum.

23. The system of claim 18, further comprising a third laser having a visible light beam propagation pathway, said pathway having an impingement location on the eye that is the same as an impingement location of the second laser beam propagation pathway.

24. The system of claim 23, wherein the third laser emits a continuous wave laser beam.

25. The system of claim 23, wherein the third laser beam has a wavelength that does not ablate corneal tissue.

26. The system of claim 23, wherein the third laser beam has a wavelength that is different than the wavelength of the second laser.

27. The system of claim 23, wherein the third laser beam wavelength is in the green part of the visible spectrum.

28. The system of claim 23, wherein the second laser and the third laser each provide a beam having a power less than 1 mW.

29. A method of shaping the cornea of the eye, the method comprising:

providing laser light having a beam propagation axis for removing eye tissue;

forming a spot of the light on the cornea; and varying the size of the spot up to a maximum size having an area that is smaller than a treatment area of the cornea and selectively controlling a scanning position of the spot on the cornea relative to a desired treatment profile within the treatment area of the cornea, wherein the size of the spot is controlled in correlation with each selectively controlled scanning position of the beam spot on the cornea.

30. The method of claim 29, wherein the varying comprises limiting the maximum size to an area between approximately 10% and approximately 90% of the treatment area.

31. The method of claim 29, wherein the varying comprises limiting the maximum size to an area between approximately 20% and approximately 80% of the treatment area.

32. The method of claim 29, wherein the varying comprises limiting the maximum size in response to the shape and size of the treatment area of the cornea.

33. The method of claim 29, further comprising physically moving the eye as an aid in providing laser light shots at different locations on the eye.

34. The method according to claim 29, further comprising providing a fixation point for a patient's eye with a visible laser light beam having a propagation path that is coincident with the laser beam propagation axis.

35. The method according claim 29, further comprising centering the laser light on a treatment axis of the eye with a visible light laser having a beam propagation path that is coincident with the laser beam propagation axis.

36. The method according to claim 35, further comprising adjusting a distance of the patient's eye from an eye surgery system by locating the eye at a point of intersection of the visible laser light and another visible laser light from a third laser with the corneal surface.

* * * * *